(12) United States Patent
Gust, Jr. et al.

(10) Patent No.: US 7,922,891 B2
(45) Date of Patent: Apr. 12, 2011

(54) METHODS FOR DETECTION AND QUANTIFICATION OF ANALYTES

(75) Inventors: John Devens Gust, Jr., Mesa, AZ (US);
Ana L. Moore, Scottsdale, AZ (US);
Thomas A. Moore, Scottsdale, AZ (US);
Alicia Brune, Tempe, AZ (US)

(73) Assignee: Arizona Board of Regents, Scottsdale, AZ (US)

( * ) Notice: Subject to any disclaimer, the term of this patent is extended or adjusted under 35 U.S.C. 154(b) by 1122 days.

(21) Appl. No.: 10/558,052

(22) PCT Filed: May 24, 2004

(86) PCT No.: PCT/US2004/016416
§ 371 (c)(1),
(2), (4) Date: Dec. 8, 2006

(87) PCT Pub. No.: WO2005/003369
PCT Pub. Date: Jan. 13, 2005

(65) Prior Publication Data
US 2007/0175770 A1      Aug. 2, 2007

Related U.S. Application Data

(60) Provisional application No. 60/473,241, filed on May 23, 2003, provisional application No. 60/473,368, filed on May 23, 2003.

(51) Int. Cl.
*G01N 27/327*      (2006.01)
*H01M 8/16*        (2006.01)
(52) U.S. Cl. ............ 205/777.5; 204/403.01; 429/401
(58) Field of Classification Search .......... 205/777.5; 204/403.01, 403.14; 429/401
See application file for complete search history.

(56) References Cited

FOREIGN PATENT DOCUMENTS
WO      WO03/079480 A1 *   9/2003
* cited by examiner

*Primary Examiner* — Kaj K Olsen
(74) *Attorney, Agent, or Firm* — Scully, Scott, Murphy & Presser, P.C.

(57) ABSTRACT

The present invention relates to a method for detecting and quantitating NADH/NAD$^+$ and/or NADPH/NADP$^+$ as well as NADH/NAD$^+$ and/or NADPH/NADP$^+$ dependent enzymes using a photoelectrochemical cell.

18 Claims, 16 Drawing Sheets

[fig. 1]
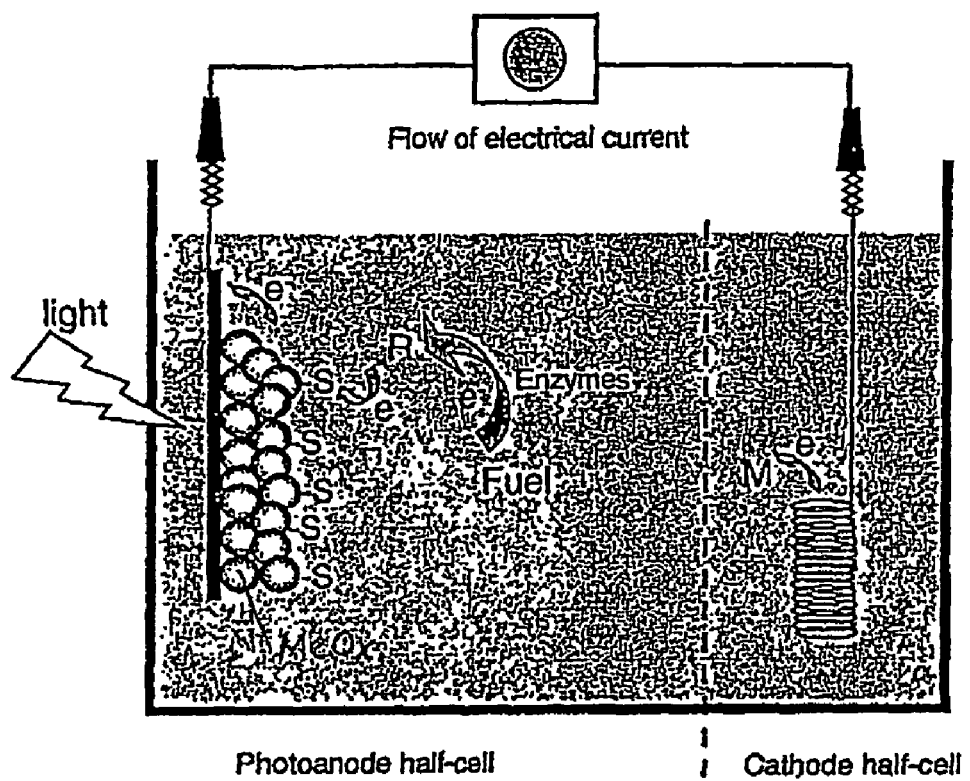

[fig. 2]
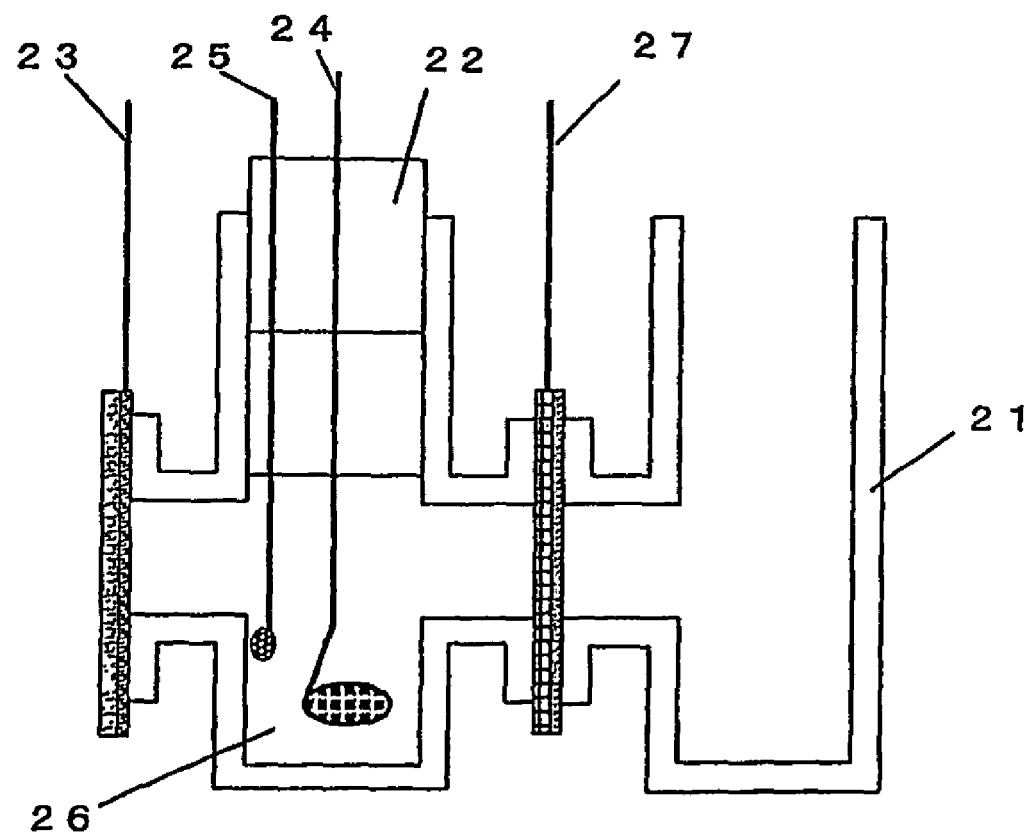

[fig. 3]
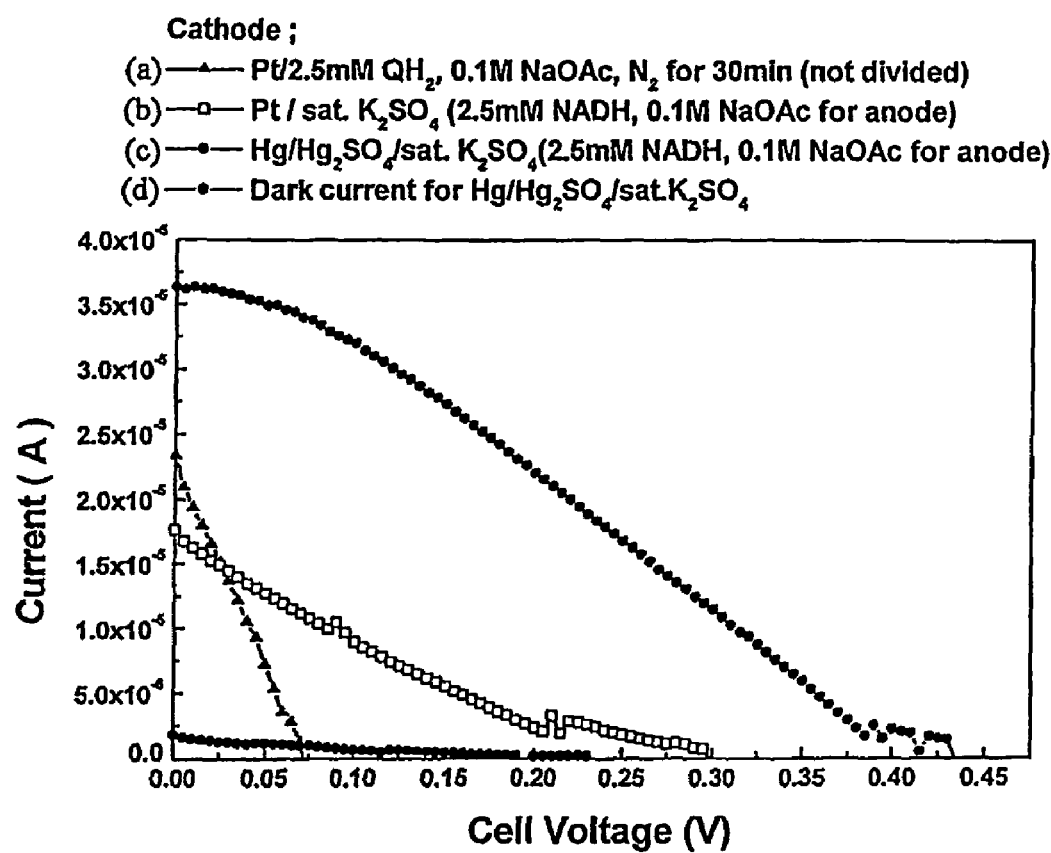

[fig. 4]
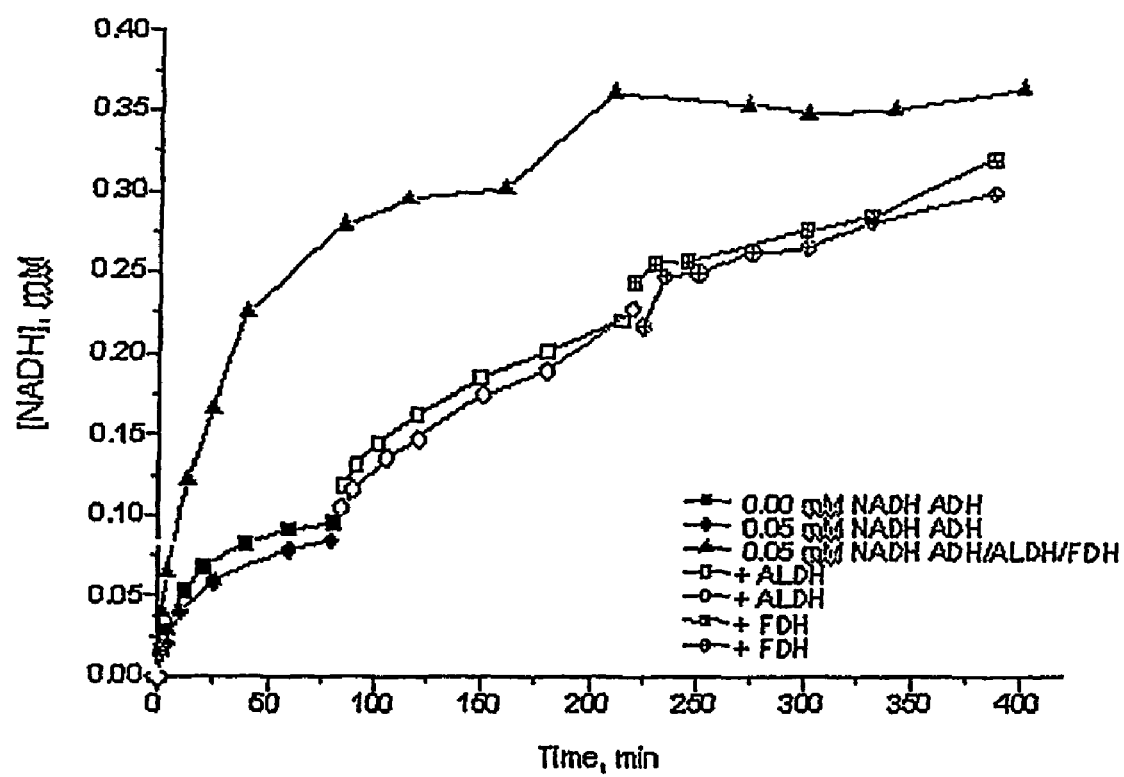

[fig. 5]
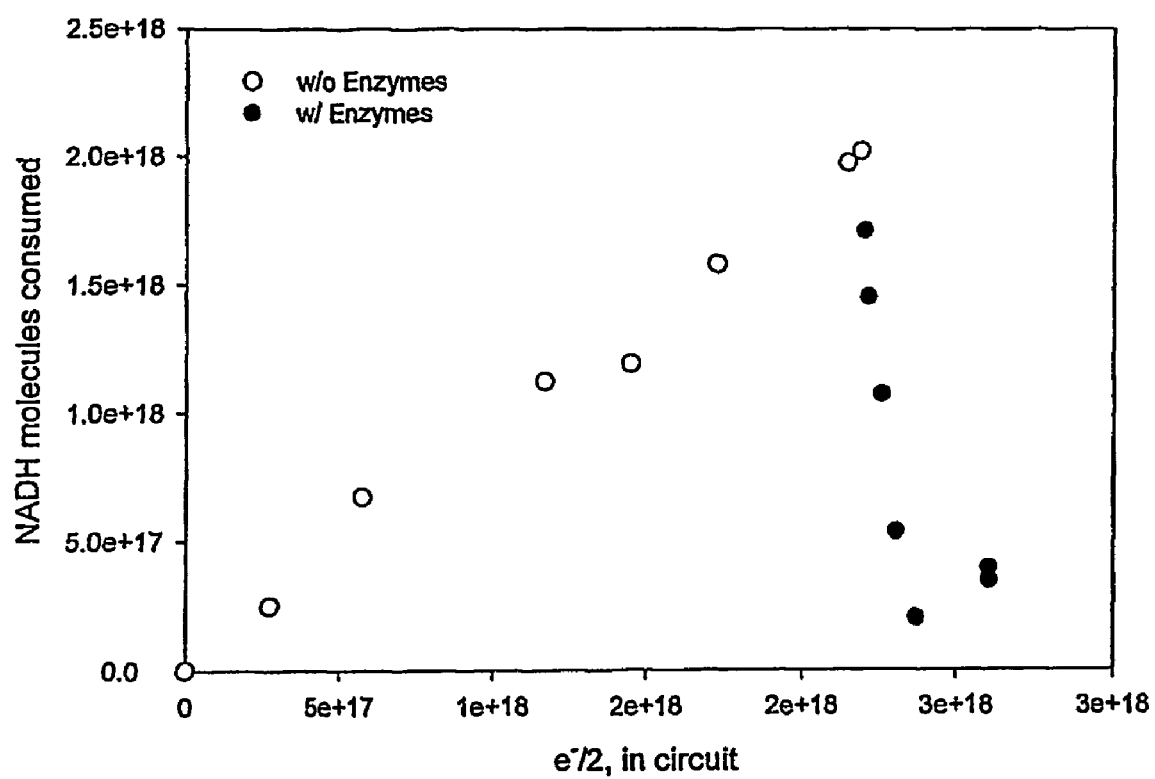

[fig. 6]
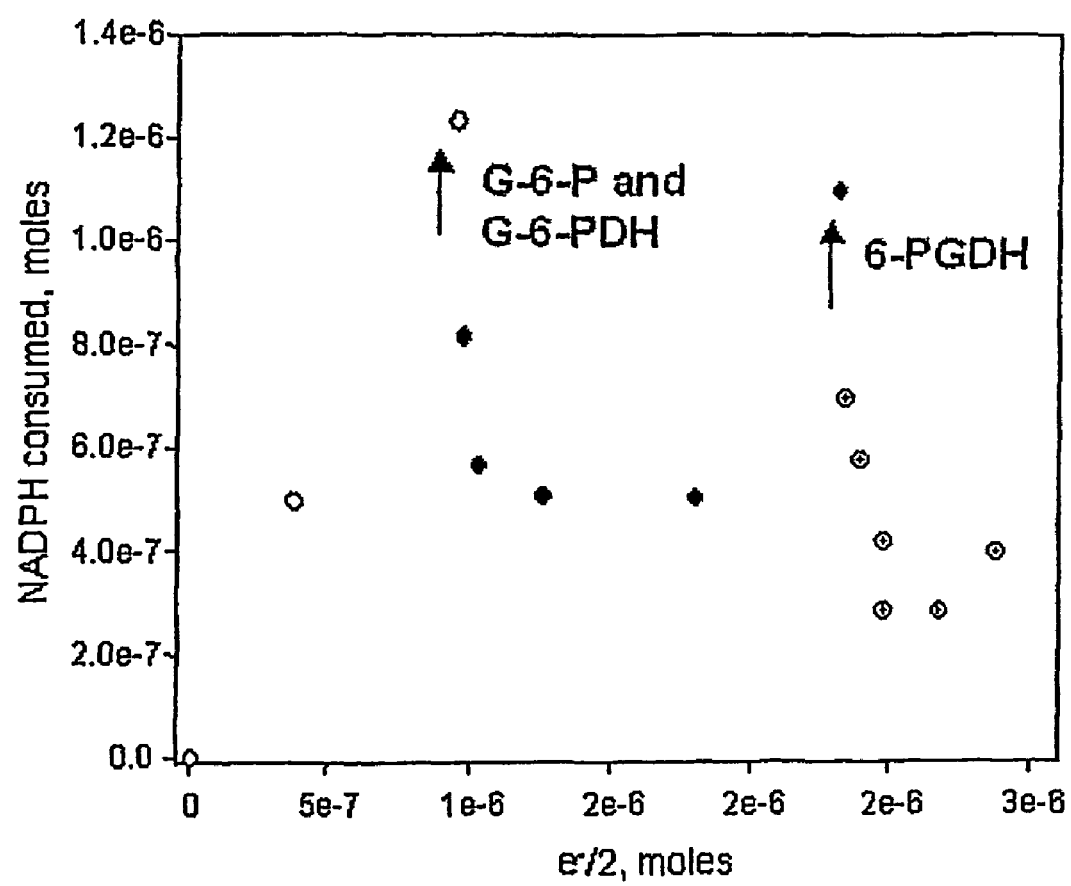

[fig.7A]
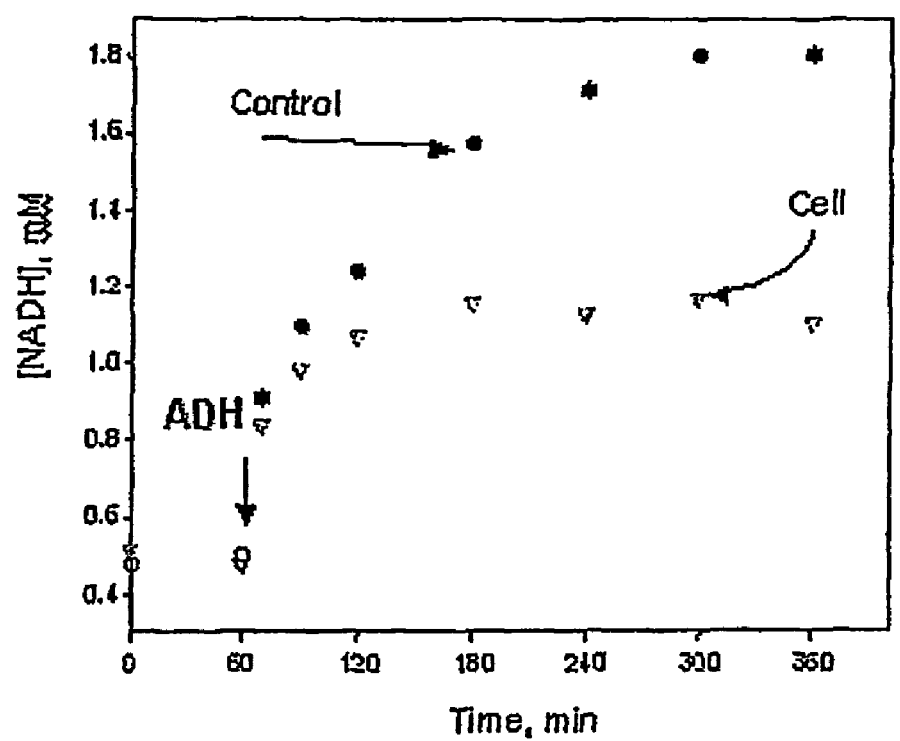

[fig.7B]
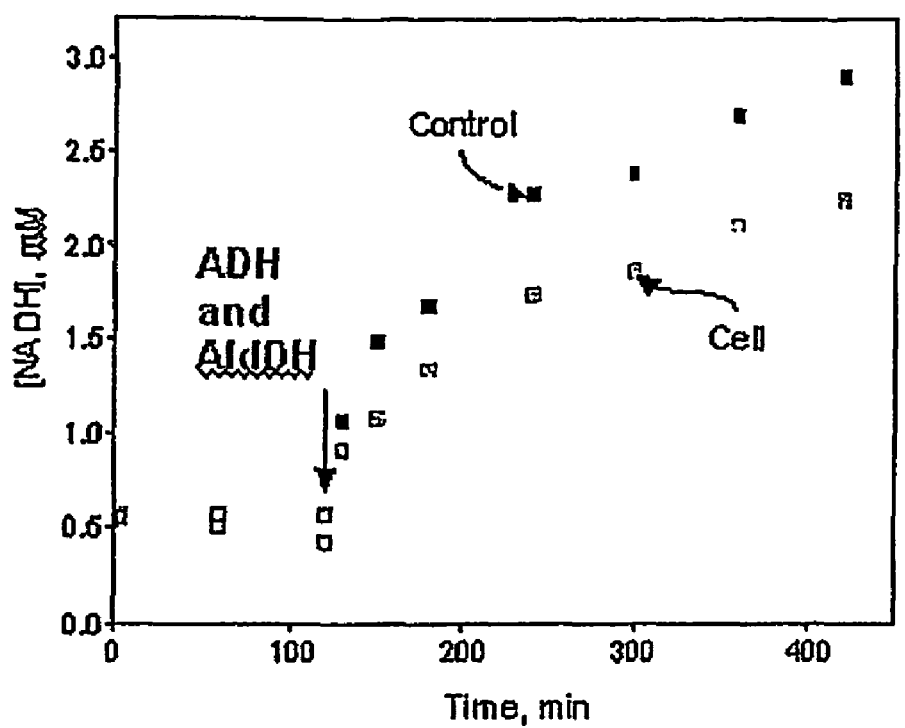

[fig. 8]
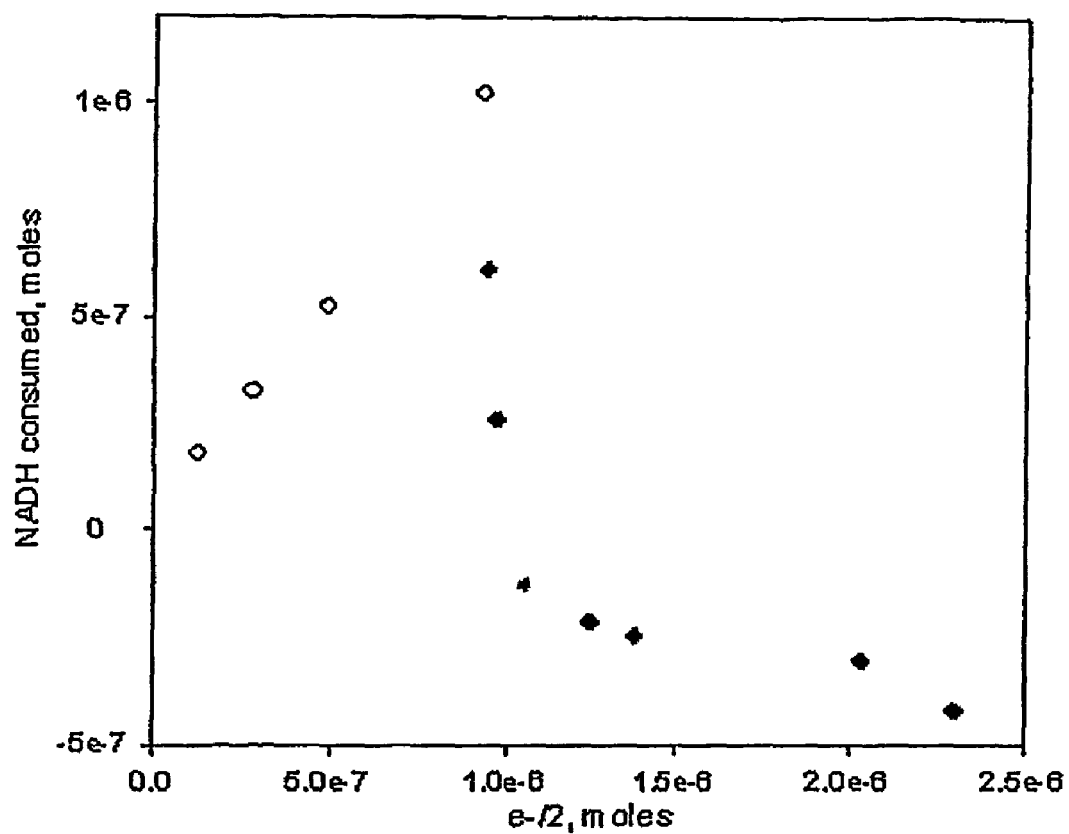

METHODS FOR DETECTION AND QUANTIFICATION OF ANALYTES

CROSS REFERENCE TO RELATED APPLICATIONS

The present application claims priority to U.S. Application No. 60/473,241 filed on May 23, 2003 and U.S. Application No. 60/473,368 filed on May 23, 2003, which applications are incorporated herein fully by this reference.

This application is a 371 National Stage Entry of PCT/US2004/016416 filed on May 24, 2004.

BACKGROUND OF THE INVENTION

During photosynthesis, plants convert light energy into electrochemical energy, and eventually into chemical potential energy stored in carbohydrates and other compounds. The carbohydrates are oxidized as needed to provide energy to the organism. A new approach to mimicry of the photosynthetic process that involves a dye-sensitized nanoparticulate semiconductor photoanode working in combination with an enzyme-catalyzed biofuel cell is described in Gust et al., "Enzyme-based Photoelectrical Cell for Electric Current Generation" (WO 03/079480). This system achieves simple and direct coupling of the two complementary processes, combines some of the advantages of each approach in a single unit, and can in principle provide more power than either process working independently.

The present inventors have now shown that this system can be used to detect and quantitate NADH/NAD$^+$ and/or NADPH/NADP$^+$ as well as NADH/NAD$^+$ and/or NADPH/NADP$^+$ dependent enzymes.

SUMMARY OF THE INVENTION

In one embodiment, the present invention relates to a method for detecting and quantifying the amount of NADH in a mixture, comprising the steps of:
  providing an electrochemical fuel cell comprising:
    a. a first electrochemical half-cell comprising a dye-sensitized nanoparticulate photoanode operating in an aqueous medium and NADH;
    b. a second electrochemical half cell comprising a suitable cathode;
    c. a device for detection of electrical current passing between the photoanode and the cathode and the associated voltage; and
    d. a suitable light source;
  illuminating the photoanode with light; and
  detecting the photocurrent flowing through the device.

In another embodiment, the present invention relates to a method for detecting and quantifying the amount of NADPH in a mixture, comprising the steps of:
  providing an electrochemical fuel cell comprising:
    a. a first electrochemical half-cell comprising a dye-sensitized nanoparticulate photoanode operating in an aqueous medium and NADPH;
    b. a second electrochemical half cell comprising a suitable cathode;
    c. a device for detection of electrical current passing between the photoanode and the cathode and the associated voltage; and
    d. a suitable light source;
  illuminating the photoanode with light; and
  detecting the photocurrent flowing through the device.

In another embodiment, the present invention relates to a method for detecting and quantifying the amount of an analyte used as a substrate by an NAD+-dependent enzyme, comprising the steps of:
  providing an electrochemical fuel cell comprising:
    a. a first electrochemical half-cell comprising a dye-sensitized nanoparticulate photoanode operating in an aqueous medium, which contains NAD+ and an enzyme that uses the analyte of interest as a substrate;
    b. a second electrochemical half cell comprising a cathode;
    c. an ammeter or other suitable device for detection of electrical current passing between the photoanode and the cathode and the associated voltage; and
    d. a suitable light source;
  illuminating the photoanode with light;
  detecting the photocurrent flowing through the device;
  adding the analyte to the photoanode;
  illuminating the photoanode with light; and
  detecting the photocurrent flowing through the device.

In another embodiment, the present invention relates to a method for detecting and quantifying the amount of an analyte used as a substrate by an NADP+-dependent enzyme, comprising the steps of:
  providing an electrochemical fuel cell comprising:
    a. a first electrochemical half-cell comprising a dye-sensitized nanoparticulate photoanode operating in an aqueous medium, which contains NADP+ and an enzyme that uses the analyte of interest as a substrate;
    b. a second electrochemical half cell comprising a cathode;
    c. an ammeter or other suitable device for detection of electrical current passing between the photoanode and the cathode and the associated voltage; and
    d. a suitable light source;
  illuminating the photoanode with light;
  detecting the photocurrent flowing through the device;
  adding the analyte to the photoanode;
  illuminating the photoanode with light; and
  detecting the photocurrent flowing through the device.

In another embodiment, the present invention relates to a method for detecting and quantifying the amount of an analyte used as a substrate by an NADH-dependent enzyme, comprising the steps of:
  providing an electrochemical fuel cell comprising:
    a. a first electrochemical half-cell comprising a dye-sensitized nanoparticulate photoanode operating in an aqueous medium, which contains NADH and an enzyme that uses the analyte of interest as a substrate;
    b. a second electrochemical half cell comprising a suitable cathode;
    c. an ammeter or other suitable device for detection of electrical current passing between the photoanode and the cathode and the associated voltage; and
    d. a suitable light source;
  illuminating the photoanode with light;
  detecting the photocurrent flowing through the device;
  adding the analyte to the photoanode;
  illuminating the photoanode with light; and
  detecting the photocurrent flowing through the device.

In another embodiment, the present invention relates to a method for detecting and quantifying the amount of an analyte used as a substrate by an NADPH-dependent enzyme, comprising the steps of:
  providing an electrochemical fuel cell comprising:
    a. a first electrochemical half-cell comprising a dye-sensitized nanoparticulate photoanode operating in a. an aqueous medium, which contains NADPH and an enzyme that uses the analyte of interest as a substrate;
b. a second electrochemical half cell comprising a suitable cathode;
c. an ammeter or other suitable device for detection of electrical current passing between the photoanode and the cathode and the associated voltage; and
d. a suitable light source;

illuminating the photoanode with light;
detecting the photocurrent flowing through the device;
adding the analyte to the photoanode;
illuminating the photoanode with light; and
detecting the photocurrent flowing through the device.

BRIEF DESCRIPTION OF THE DRAWINGS

By way of example and to make the description more clear, reference is made to the accompanying drawings in which:

FIG. 1 is a schematic diagram illustrating the procedure of photoelectrochemical oxidation of a carbon-containing compound (fuel) by a photosensitizer (S) in the presence of an enzyme and an oxidation-reduction mediator (R).

FIG. 2 is a diagram illustrating the structure of a power-generating cell used in the evaluation of the photoelectrochemical properties and battery properties, wherein the reference numeral 21 indicates a power-generating cell, the reference numeral 22 indicates a silicon plug, the reference numeral 23 indicates a negative electrode, the reference numeral 24 indicates a counter electrode, the reference numeral 25 indicates a reference electrode, the reference numeral 26 indicates an electrolyte, and the reference numeral 27 indicates an air electrode.

FIG. 3 is a diagram illustrating the current-voltage characteristics of the power-generating cell.

FIG. 4 is a diagram illustrating the change of NADH concentration with time a solution containing various combinations of enzymes and methanol.

FIG. 5 is a diagram illustrating the relationship between the amount of NADH consumed in the electrolyte in the power-generating cell and the amount of electrons removed from the power-generating cell by the external circuit.

FIG. 6 is a diagram illustrating the relationship between the consumed amount of NADPH in the electrolyte in the power-generating cell and the amount of electrons removed from the power-generating cell by the external circuit.

FIG. 7A is a diagram illustrating the change of NADH concentration with time in the electrolyte in the power-generating cell; FIG. 7B is a diagram illustrating the change of NADH concentration with time in the electrolyte in the power-generating cell.

FIG. 8 is a diagram illustrating the relationship between the amount of NADH consumed in the electrolyte in the power-generating cell and the amount of electrons taken out of the power-generating cell by the external circuit.

DETAILED DESCRIPTION OF THE INVENTION

Figure 9:
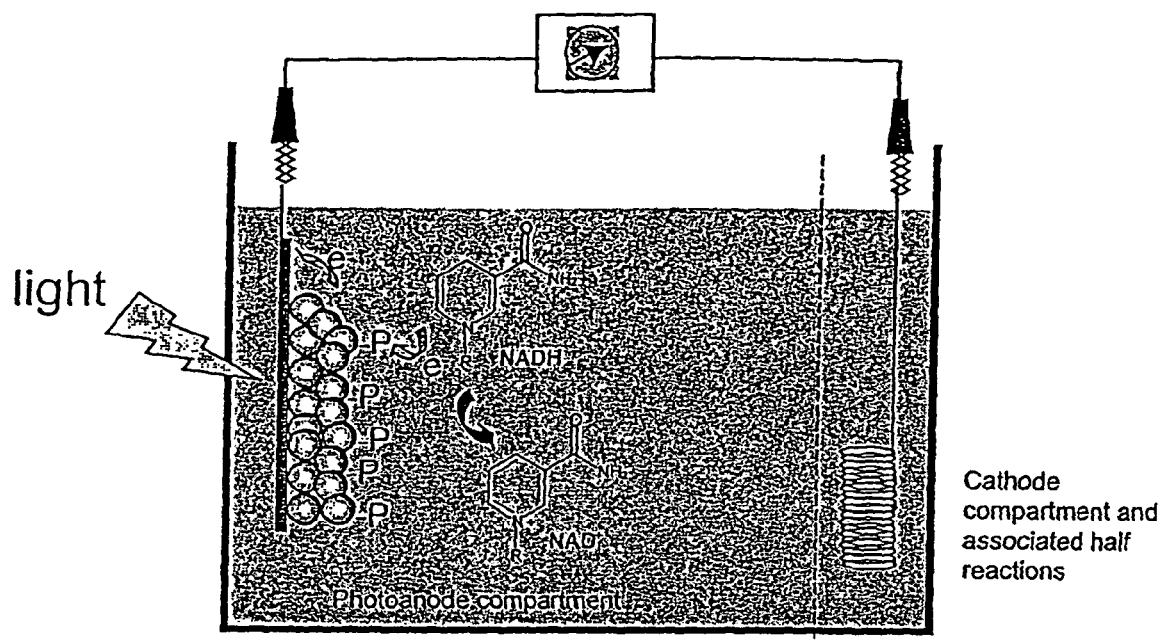
FIG. 9 is a schematic diagram illustrating a photoelectrochemical cell useful for the detection of NADH or NADPH.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing, for example, the compositions and methodologies that are described in the publications which might be used in connection with the presently described invention. The publications listed or discussed above, below and throughout the text are provided solely for their disclosure prior to the filing date of the present application. Nothing herein is to be construed as an admission that the inventors are not entitled to antedate such disclosure by virtue of prior invention.

In one embodiment, the present invention is directed to a method for electrical detection and quantification of nicotinamide adenine dinucleotide, reduced form (NADH) or nicotinamide adenine dinucleotide phosphate, reduced form (NADPH). NADH and NADPH are enzyme cofactors that are produced by, or consumed by, a large variety of enzymes. By detecting and quantifying the amount of NADH or NADPH present in a mixture containing such enzymes, it is possible to quantify the activity of the enzyme, or the amount of enzyme substrate that was initially present in the mixture, and that was converted to product by the enzyme. Thus, the detection and quantification of NADH and NADPH indirectly detects and quantifies the amount of enzyme substrate that was present. NADH and NADPH concentrations are currently often determined by light spectroscopic methods. These methods are subject to interference by other materials that absorb light at the same wavelengths. The method described here is much more specific. It would be useful in a variety of medical and biotechnological applications.

In another embodiment, the invention is directed to a method for detecting and quantiing substrates (analytes) of NADH/NAD$^+$ or NADPH/NADP$^+$ dependent enzymes. It is based on the fact that in such enzymes, consumption of the substrate through enzyme activity is proportional to consumption of the coenzyme NADH, NAD$^+$, NADPH, or NADP$^+$. In this method, the analyte, enzyme, and coenzyme are placed in a photoelectrochemical cell. The enzyme converts the substrate analyte to its product, and in the process consumes the coenzyme. The amount of coenzyme consumed, and thus the amount of analyte originally present, is determined photoelectrochemically. This method has the advantages of an electrical output, extreme specificity, and freedom from interferences that are common to optical absorption methods.

Overview of the Invention. The present inventors have shown that a photofuel cell, described below, initially developed to provide electricity, can be used as a sensor for analytes of biotechnological and biomedical importance. For example, it can be used as a sensor or detecting and quantifying the common coenzymes NADH, NAD$^+$, NADPH, and NADP$^+$ or as a sensor for detecting and quantifying the substrates of enzymes dependent upon the coenzymes.

When NADH is absent in the photoelectrochemical cell, *P donates electrons to nanoparticle, generating P$^+$. Recombination occurs, and no net current flows. When NADH is present, *P donates electrons to nanoparticle, generating P$^+$. P$^+$ is reduced by NADH, ultimately yielding NAD$^+$ and regenerating P. Electrons flow from photoanode to cathode, generating current and voltage. Thus, the photocell detects the presence of NADH.

At low concentrations of NADH, the photocurrent at low conversion of NADH to NAD$^+$ is a function of the original NADH concentration, as is the open circuit photovoltage. At any initial NADH concentration, the NADH can be totally consumed by the cell. When this occurs, the total number of electrons flowing through the external circuit equals twice the total number of NADH molecules initially present. Thus, the current flow provides a measure of the number of NADH molecules consumed.

The photoelectrochemical cell also acts as a sensor or NADPH. NADPH is used by the cell in the same way as NADH. Thus, the concentration of NADPH can be determined by the current-voltage characteristics of the cell, or by integrating the total number of electrons passing through the external circuit, just as in the case of NADH.

Enzymes are highly specific, operating on only one, or a few, substrates. Enzyme reactions do not produce side products: all substrate is converted to a single product suite. Also, enzymes can interact with substrate at very low concentrations. But, there are problems with enzymes as sensor elements. Different substrates yield different products, so a sensor for each product must be developed. Also, products are not necessarily more easily detected than substrates. If so, the enzymatic action does not contribute to sensor function.

Dehydrogenase enzymes are one example of sensor elements. At least 250 different dehydrogenase enzymes exist. Most of these enzymes use NADH or NADPH as cofactors. Usually, one NADH or NADPH molecule is consumed for each substrate molecule consumed. As described below, NAD(P)H can be detected by the photofuel cell. If one measures the amount of NAD(P)H produced, one has measured the amount of substrate initially present.

Photoelectrochemical Cell

A photoelectrochemical cell suitable for practice of the present invention as been described in Gust et al., WO 03/079480 ("Enzyme-based Photoelectrochemical Cell for Electric Current Generation"), the entire contents of which are hereby incorporated by reference. The photoelectrochemical cell includes a positive electrode and a negative electrode provided as constituents with an electrolyte interposed between them. When the negative electrode receives electrons from a carbon-containing fuel compound via a photosensitizer compound which produces an oxidant and electrons when irradiated with light, an oxidation-reduction mediator which supplies electrons to the oxidized photosensitizer molecule, and enzymes that catalyze oxidation of the carbon-containing fuel compound, an electromotive force is generated across the positive electrode and the negative electrode. This makes it possible to utilize chemical energy accumulated in the carbon-containing compound directly as electrical energy in a form biased by light radiation energy.

FIG. 1 illustrates a schematic diagram of the configuration of a photobiological fuel. FIG. 1 illustrates how electrons (E−) which have been possessed by a carbon-containing compound (fuel) are released from the carbon-containing compound and ultimately flow through an external electric circuit (load) from the negative electrode to the positive electrode. The electron flow within the cell occurs via a photosensitizer compound (S) retained in or on an oxide semiconductor (MeOx) shown in a spherical form. When irradiated with light, sensitizer S produces an excited state S*. The excited state S* injects an electron into the semiconductor, leaving an oxidant S$^+$. The electron (E$^-$) has been biased by light irradiation to the optical excitation energy of S (the difference in energy between S and S*). The electron does work in the external circuit, and reaches the positive electrode, where it is used in a reduction reaction with material M. In this manner, an electromotive force is generated across the positive electrode and the negative electrode, generating electricity. During the process, the oxidized photosensitizer S$^+$ is reduced to its original form by a redox mediator R, generating R in an oxidized form. The enzyme (s) reduce the oxidized redox mediator back to its original form, obtaining the necessary electrons from oxidation of the carbon-containing fuel compounds. Thus, neither photosensitizer S nor redox mediator R are consumed.

The photosensitizer compound S, which produces an oxidant S$^+$ and an electron when irradiated with light, is disposed on an oxide semiconductor. This compound may have a single light absorption peak or a plurality of light absorption peaks in a wavelength range of ~300 nm to ~1,000 nm. Such a compound may be a metal complex dye, organic dye, or the like. Examples of a metal complex dye are ruthenium complex dyes or platinum complex dyes having biquinoline, bipyridyl, phenanthroline, or thiocyanic acid or derivatives thereof as ligands. Examples of organic dyes which may also contain metal atoms are porphyrin-based dyes having a single porphyrin ring or a plurality of porphyrin rings. The porphyrin rings may be metal free, or contain zinc (Zn), magnesium (Mg), or the like as a central atom. Examples of such a porphyrin-based dye include those represented by the general formulae P1 to P6 below. Examples of organic dyes are 9-phenylxanthene-based dyes, merocyanine-based dyes, polymethine-based dyes, or the like. In particular, the compound P1, 5-(4-carboxyphenyl)-10,15,20-(4-methylphenyl) porphyrin, having the structure shown below has a high light absorption efficiency and also high affinity for the oxide semiconductor so that it cannot be easily eluted with the electrolyte and thus can be kept stable even after a prolonged contact with the electrolyte. Further, since generation of excited electrons from the compound P1 by irradiation with light can occur over a prolonged lifetime, the compound P1 can exhibit high photoelectric conversion efficiency to advantage. The disposition of a compound which produces an oxidant and an electron when irradiated with light on an oxide semiconductor makes it possible to quickly move an excited electron produced by irradiation with light to the oxide semiconductor and makes less likely the recombination of the oxidant and excited electron produced by irradiation with light, thereby keeping the efficiency of reception of electrons from the carbon-containing compound into the external electrical circuit higher.

As the oxide semiconductor, tin dioxide ($SnO_2$), titanium dioxide ($TiO_2$), zinc oxide (ZnO), tungsten oxide ($WO_3$) or composites thereof such as $TiO_2$-$WO_3$ may be used.

P1

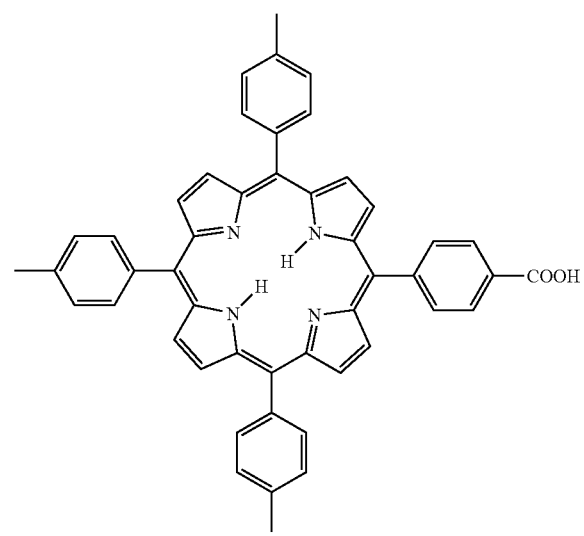

P2

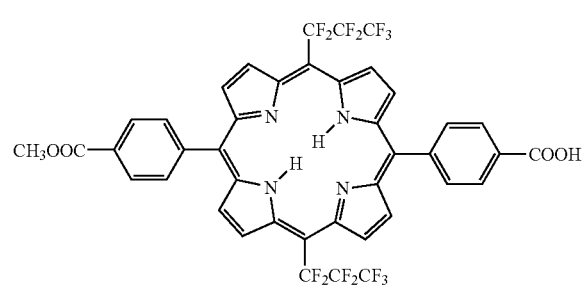

P3

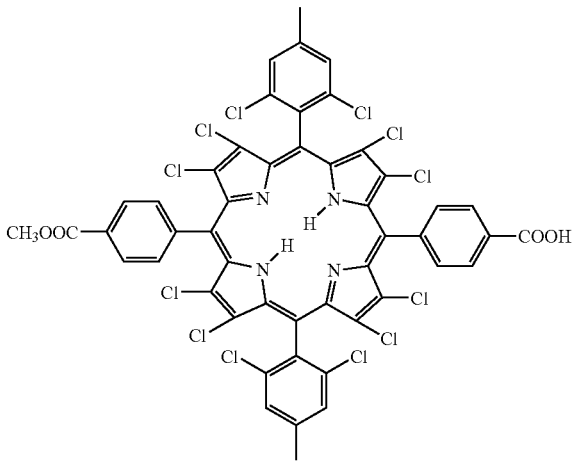

P4

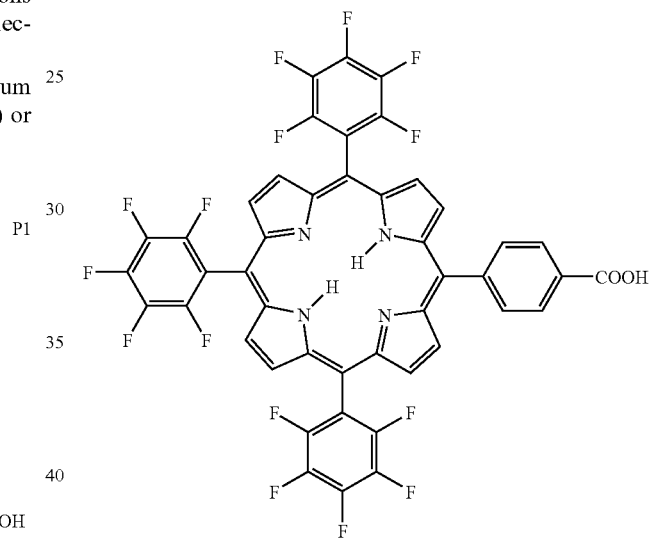

P5

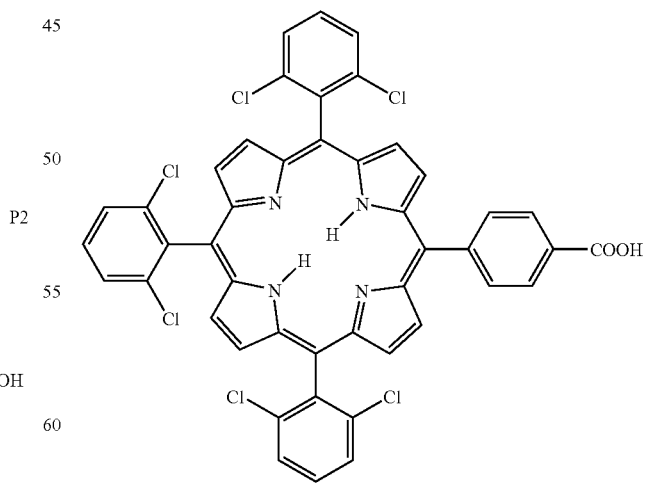

-continued

P6

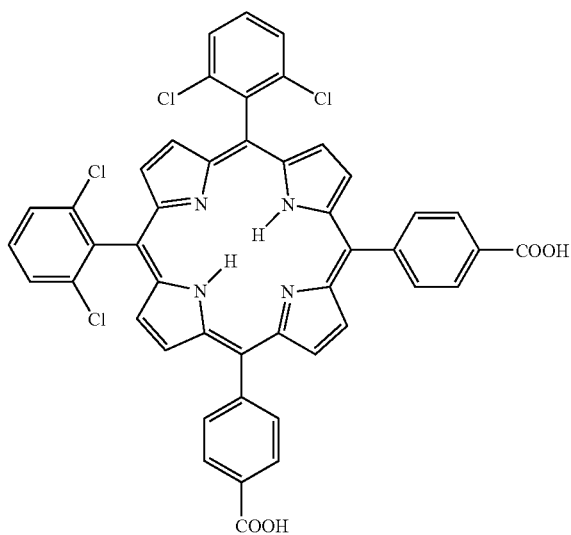

Examples of the carbon-containing fuel compound used in photoelectrical fuel cells, which may be one that is cyclically regenerated in a natural biosphere, include carbohydrates (e.g., sugars, starches), lipids, hydrocarbons, alcohols, aldehydes and organic acids. Such compounds can be produced from carbon dioxide gas and water by photosynthesis and then accumulated. The solar energy stored in these compounds is used as chemical energy via the metabolism of a organism, producing carbon dioxide gas. This forms a clean cyclic system.

Examples of the oxidation-reduction mediator (R) which receives electrons from the carbon-containing fuel compound through the mediation of enzymes and supplies electrons to the oxidant ($S^+$) produced by irradiation with light to regenerate the original photosensitizer compound (S) are a quinone/hydroquinone oxidation-reduction couple, the $NAD^+$/NADH oxidation-reduction couple, the $NADP^+$/NADPH oxidation-reduction couple, the $I_2/I_3^-$ oxidation-reduction couple, and metal proteins having an oxidation-reduction capacity such as ferredoxin and myoglobin.

The enzymes, which catalyze the transfer of electrons from the carbon-containing fuel compound to an oxidized form of the oxidation-reduction mediator R, are not specifically limited. In practice, however, dehydrogenase enzymes may be used singly or in combination depending on the kind of the carbon-containing fuel compound. In the case where the fuel is glucose, an enzyme system containing at least glucose dehydrogenase (GDH) may be used.

In the case where the fuel is D-glucose-6-phosphate, an enzyme system containing at least D-glucose-6-phosphate dehydrogenase (G-6-PDH) or at least G-6-PDH and 6-phosphogluconate dehydrogenase (6-PGDH) may be used.

In the case where the fuel is methyl alcohol, an enzyme system containing at least an alcohol dehydrogenase (ADH), an enzyme system containing at least ADH and an aldehyde dehydrogenase (ALDH), or an enzyme system containing at least ADH, ALDH and a formate dehydrogenase (FDH) may be used.

In the case where the fuel is ethyl alcohol, an enzyme system containing at least an alcohol dehydrogenase (ADH) or an enzyme system containing at least ADH and an aldehyde dehydrogenase (ALDH) may be used. In the case where a plurality of fuels is used, enzymes corresponding to these fuels may be used in admixture.

As the electrolyte to be incorporated into the photobiological fuel cell, there may be used any material regardless of whether it is an organic material, inorganic material, liquid or solid so far as it allows the movement of anions and/or cations from the positive electrode to the negative electrode and/or from the negative electrode to the positive electrode to cause continuous progress of oxidation-reduction reactions at the positive electrode and the negative electrode. An aqueous solution obtained by dissolving a salt such as KCl, NaCl, $MgCl_2$, $NH_4Cl$ and $Na_2PO_4$, an alkali such as $NH_4OH$, KOH and NaOH or an acid such as $H_3PO_4$ and $H_2SO_4$ in water is safe, causes no environmental pollution, and can be easily handled to advantage. Alternatively, a solution of a quaternary ammonium salt such as pyridinium iodide, a lithium salt such as lithium iodide, an imidazolium salt such as imidazolinium iodide, t-butylpyridine or the like in acetonitrile, methoxyacetonitrile or methoxypropionitrile, an ion exchange membrane made of a polymer material such as fluororesin having sulfonic acid groups, amide groups, ammonium groups, pyridinium groups or the like or a polymer electrolyte such as solution of a salt such as $LiBF_4$, $LiClO_4$ and $(C_4H_9)_4NBF_4$ in a polypropylene oxide, polyethylene oxide, acrylonitrile, polyvinylidene fluoride, polyvinyl alcohol or the like may be used.

The reaction at the positive electrode in the photobiological fuel cell of the invention involves a reduction reaction occurring at a higher (or more anodic) potential than that of the electron taken out of the carbon-containing compound via an optically excited active species ($S^*$) of molecule at the negative electrode. Any reduction reaction can be employed so far as the electron thus taken out is electrochemically received by the positive electrode via the external load.

Examples of the reaction at the positive electrode include reduction reactions of water or oxygen, reduction reactions of hydroxide or oxides such as NiOOH, MnOOH, $Pb(OH)_2$, PbO, $MnO_2$, $Ag_2O$, $LiCoO_2$, $LiMn_2O_4$ and $LiNiO_2$, reduction reactions of sulfides such as $TiS_2$, $MoS_2$, FeS and $Ag_2S$, reduction reactions of metal halides such as AgI, $PbI_2$ and $CuCl_2$, reduction reactions of halogen such as $Br_2$ and $I_2$, reduction reactions of organic sulfur compounds such as quinone and organic disulfide compounds, and reduction reactions of electrically-conductive polymers such as polyaniline and polythiophene.

In particular, the positive electrode is preferably an oxygen electrode for reducing oxygen. In this arrangement, a gas containing oxygen can be used as the positive active material, eliminating the necessity of retaining a positive active material in the battery and hence making it possible to form a battery having a higher energy density.

Any material capable of reducing oxygen may be used as the oxygen electrode. Examples of such an oxygen-reducing material include activated charcoal, manganese oxide including $MnO_2$, $Mn_3O_4$, $Mn_2O_3$ and $Mn_5O_8$, platinum, palladium, iridium oxide, platinum-ammine complexes, cobalt-phenylenediamine complexes, metal porphyrins (metal: cobalt, manganese, zinc, magnesium, etc.), and perovskite oxides such as La (Ca) $CoO_3$ and $La(Sr)MnO_3$.

Example 1 of a Photoelectrical Chemical Cell (from Gust et al., WO 03/079480)

As a photosensitizer compound which produces an oxidant and an electron when irradiated with light, 5-(4-carboxyphenyl)-10,15,20-(4-methylphenyl) porphyrin (P1) was used as a typical representative of a porphyrin photosensitizer used to prepare a negative electrode.

Preparation Of The Negative Electrode. A light-transmitting glass substrate with a thickness of 1 mm bearing a thin film of electrically conducting indium-tin oxide (ITO) with a surface resistivity of 10-12 $\Omega/cm^2$ was used to prepare the negative electrode. A 1% by weight aqueous dispersion of particulate tin dioxide ($SnO_2$) having an average particle diameter of 10 nm was deposited on the ITO film by spraying or otherwise applying layers over a hot plate. The electrode was dried at a temperature of 80° C., and then sintered at a temperature of 400° C. in air for 1 hour to form a film of particulate $SnO_2$. Subsequently, the electrode was dipped into a 1-5 mM solution of photosensitizer P1 (dissolved in dichloromethane, toluene, or hexanes) for typically 1 hour, withdrawn from the solution, washed with clean solvent, and dried with a stream of nitrogen gas. The presence of P1 on the electrode particulate surface was confirmed by its absorption spectrum.

Assembly Of Test Cell. The negative electrode thus prepared was then used to assemble a power-generating cell 21 having the structure shown in FIG. 2.

In the power-generating cell 21, the film of particulate $SnO_2$ on the negative electrode 23 on which the dye P1 is deposited comes in contact with an electrolyte 26. In the electrolyte 26 are disposed a counter electrode 24 which forms a battery in combination with the negative electrode 23 and a reference electrode 25 which gives a reference potential on the basis of which the potential of the negative electrode 23 is measured. Further disposed is an air electrode 27, which forms a battery in combination with the negative electrode 23 instead of the counter electrode 24. The air electrode 27 was prepared by embedding a mixture of $Mn_2O_3$ powder, activated charcoal powder, acetylene black powder and polytetrafluoroethylene (PTFE) binder on a nickel screen having a thickness of 0.2 mm. The reference numeral 22 indicates a silicon plug for fixing the counter electrode 24 and the reference electrode 25 to the power-generating cell 21.

Operating Characteristics Of Photoelectric Power-Generating Cell. A power-generating cell (a) was assembled as described above, using the negative electrode 23, a platinum (Pt) counter electrode (24), and an electrolyte 26, which is a 0.1 M aqueous solution of sodium acetate (NaOAc) containing 2.5 mM hydroquinone ($QH_2$) as an oxidation-reduction mediator (R).

A power-generating cell (b) was assembled as described above, using the negative electrode 23, a platinum (Pt) counter electrode 24 immersed in a saturated aqueous solution of potassium sulfate free of dissolved oxygen and isolated from the electrolyte 26 by an ion-permeable membrane, and electrolyte 26, which is a 0.1 M aqueous solution of sodium acetate (NaOAc) containing 2.5 mM nicotinamide-adenine dinucleotide in the reduced form (NADH) as an oxidation-reduction mediator (R).

A power-generating cell (c) was assembled as described above, using the negative electrode 23, a counter electrode 24, which is a mercury/mercury (I) sulfate electrode separated from electrolyte 26 by an ion permeable membrane, and electrolyte 26, which is an 0.1 M aqueous solution of sodium acetate containing 2.5 mM nicotinamide-adenine dinucleotide in the reduced form (NADH) as an oxidation-reduction mediator (R).

FIG. 3 illustrates current-voltage characteristics of these power-generating cells developed when they are irradiated with light having a wavelength of 520 nm. In FIG. 3, the curves (a), (b) and (c) indicate the current-voltage characteristics of the power-generating cells (a), (b) and (c), respectively. All the power-generating cells (a), (b) and (c) work as batteries, although they show differences in current-voltage characteristics. In FIG. 3, the curve (d) indicates the current-voltage characteristics of the power-generating cell (a) developed when it is not irradiated with light. When not irradiated with light, a power-generating cell gives little or no output current.

In these cells, the dye deposited on the negative electrode acts as a photosensitizer compound (S) which upon irradiation produces an excited state (S*). In contact with the metal oxide, it injects an electron into the oxide particle, producing an oxidant ($S^+$). The external circuit removes the electron thus produced, where it is then measured as output current of the battery. In cells of type (c), the oxidant ($S^+$) receives an electron from the oxidation-reduction mediator NADH (or in some cases $QH_2$), regenerating S. Thus, in a cell lacking enzymes or carbon-containing fuel compounds, the supply of electrons to the external circuit lasts until NADH (or $QH_2$ when that is used as the oxidation-reduction mediator) is consumed.

An assay (not performed in the cell) was done to test the production of NADH when $NAD^+$ is present and methanol is used as the carbon-containing fuel compound. An aqueous solution of pH 8.0 containing 1 M NaCl, 5 mM oxidized nicotinamide-adenine-dinucleotide ($NAD^+$) and methanol with 0.0 and 0.05 mM reduced nicotinamide-adenine-dinucleotide (NADH) and an alcohol dehydrogenase (ADH), an aldehyde dehydrogenase (ALDH) and a formate dehydrogenase (FDH) as enzymes added thereto. The change of NADH concentration with time during irradiation with light is shown in FIG. 4.

In FIG. 4, the symbol ▲ indicates the change of NADH concentration in a solution having 5.0 mM $NAD^+$, 0.05 mM NADH, ADH, ALDH and FDH added thereto. The symbol ● indicates the change of NADH concentration in a solution having 5 mM $NAD^+$, 0.05 mM NADH and ADH added thereto. The symbol ○ indicates the change of NADH concentration in the same solution as in (●) but having AILDH added thereto after the lapse of a predetermined time from the addition of NADH and ADH. The symbol ○+ indicates the change of NADH concentration in the solution (○) but having FHD added thereto after the lapse of a predetermined time from the addition of NADH, ADH and ALDH. The symbol ■ indicates the change of NADH concentration in the electrolyte having 5 mM $NAD^+$ and ADH added thereto. The symbol □ indicates the change of NADH in the same solution as the solution ■ but having ALDH added thereto. The symbol □+ indicates the change of NADH in the same solution as the electrolyte □ but having FDH added thereto. All these tests were observed to have an increase of NADH concentration, demonstrating that an electron moves from methanol to $NAD^+$ through the mediation of the enzyme to produce NADH. In other words, as shown in FIG. 4, NADH is formed from $NAD^+$ through the mediation of enzymes that utilize methanol. These results imply that as long as methanol is present in a power-generation cell with the mediation of enzymes, NADH used by the negative electrode will be regenerated, and power generation can be maintained under irradiation with light.

FIG. 5 is a graph illustrating the relationship between the amount of electrons taken out of the cell by the external circuit (abscissa) and the amount of NADH consumed by irradiation with light (ordinate) in a power-generating cell of type (c), with the electrolyte 26 containing NADH and methanol. The symbol ○ indicates the relationship between the amount of NADH consumed and the amount of electrons produced in the external circuit when the electrolyte is free of enzymes. This relationship shows that the consumed amount of NADH and the amount of electrons are proportional to each other, demonstrating that electrons released from NADH are properly taken out by the external circuit. The symbol ● indicates the relationship between the amount of NADH consumed and the amount of electrons produced in the external circuit when ADH, ALDH and FDH are added to the electrolyte as the enzyme system. Under these conditions, little or no NADH is consumed, regardless of the amount of electrons removed by the external circuit. In other words, NADH releases electrons to form NAD$^+$, which then receives electrons from methanol through the mediation of the enzymes thus added to regenerate NADH. This state of little or no NADH consumption lasts as long as methanol is present in the electrolyte. In other words, power generation continues while methanol is present.

In these and other experiments, the concentration of NADH in the electrolyte was determined by the intensity of the peak present in the vicinity of 340 nm in the UV absorption spectrum of NADH.

In the present example, tin oxide ($SnO_2$) was used as the oxide semiconductor. The same evaluation was made with particulate $TiO_2$, and could be made with films of particulate metal oxide such as ZnO and $TiO_2$—$WO_3$ instead of $SnO_2$. The same evaluation using $SnO_2$ was also made on the compounds P2, P3, P4, P5 and P6 instead of the compound P1 as a photosensitizer. These compounds also produce an oxidant and an electron when irradiated with light. As a result, these power-generating cells will exhibit operating characteristics similar to that of P1.

Example 2 of a Photoelectrical Chemical Cell (from Gust et al., WO 03/079480)

A power-generating cell was formed by the same type of negative electrode 23 as used in Example 1, platinum (Pt) as counter electrode 24 and an aqueous buffered solution at pH 8.0 containing NADP$^+$/NADPH as the oxidation-reduction mediator in the electrolyte. D-Glucose-6-phosphate (G-6-P) was used as a carbon-containing fuel compound. D-glucose-6-phosphate dehydrogenase (G-6-PDH) and 6-phosphogluconate dehydrogenase (6-PGDH) were used as an enzyme system.

FIG. 6 is a graph illustrating the relationship between the amount of electrons removed by the external circuit from the electrolyte (abscissa) and the amount of NADPH consumed during irradiation with light (ordinate). The symbol ○ indicates the relationship between the amount of NADPH consumed and the amount of electrons injected into the external circuit with an the electrolyte free of fuel and enzyme. This relationship shows that the amount of NADPH consumed and the amount of electrons produced are proportional to one another, demonstrating that electrons released from NADPH are removed by the external circuit. The symbol ● indicates the relationship between the amount of NADPH consumed and the amount of electrons removed in the electrolyte to which has been added G-6-P as a carbon-containing fuel compound, and the enzyme G-6-PDH. The amount of NADPH consumed is greatly reduced. This result shows that NADPH has released electrons to form NADP$^+$, which then receives electrons from G-6-P to regenerate NADPH through the mediation of the added enzymes. The amount of NADPH consumed remains approximately constant regardless of the number of electrons removed by the external circuit. This state lasts as long as G-6-P is present in the electrolyte. At later times, when G-6-P is entirely oxidized to gluconolactone-6-phosphate, the amount of NADPH consumed again rises. The gluconolactone-6-phosphate hydrolyzes in the electrolyte to 6-phosphogluconate (6-PG). The amount of NADPH consumed increases in proportion to the amount of electrons removed into the external circuit. When 6-PGDH, which is an enzyme that oxidizes 6-PG, is added to the electrolyte, the amount of NADPH consumed shows a sudden drop as shown by the symbol ○+ in FIG. 6. Electrons are again supplied by 6-PG, which is a fuel, to regenerate NADPH. The reception of electrons by the external circuit lasts as long as 6-PG is present in the electrolyte.

In this example, the oxide semiconductor was tin oxide ($SnO_2$). Similar evaluations could be made on films of particulate $TiO_2$ or other particulate metal oxides such as ZnO and $TiO_2$-$WO_3$.

Example 3 of a Photoelectrical Chemical Cell (from Gust et al., WO 03/079480)

A power-generating cell was formed by the same negative electrode 23 as used in Example 1, platinum (Pt) as a counter electrode 24 and a buffered solution at pH 8.0 containing a 0.5 mM NADH and 10 mM NAD+ as an electrolyte. Ethanol ($CH_3CH_2OH$) was used as a carbon-containing fuel compound. The nicotinamide-adenine-dinucleotide couple (NADH)/(NAD$^+$) was used as the oxidation-reduction mediator. An alcohol dehydrogenase (ADH) and an aldehyde dehydrogenase (ALDH) were used as an enzyme system.

FIG. 7A is a graph illustrating the change of NADH concentration with time in the electrolyte containing ethanol. An alcohol dehydrogenase (ADH) enzyme system was added thereto after 60 minutes. In FIG. 7A, the symbol ▼ indicates the change of NADH concentration in the power-generating cell containing ethanol and ADH. The concentration of NADH increases with light irradiation time until it reaches a value determined by the amount of electrons removed by the external circuit and the amount of ethanol in the electrolyte. On the contrary, the symbol ● indicates the change of NADH concentration in an identical electrolyte put in a container free of electrodes, but having ADH added thereto under the same conditions as in the power-generating cell. In FIG. 7A, these data are noted as "Control". Since the Control has no electrodes, electrons are not removed by the external circuit. The NAD$^+$ in the electrolyte receives electrons from ethanol and is converted to NADH through the mediation of ADH. Thus, the concentration of NADH continues to increase with time.

A power-generating cell was formed by a negative electrode 23, an air electrode 27 and an electrolyte at pH 8 containing ethanol, NADH and ADH as an enzyme system. When irradiated with sunlight, the power-generating cell operated as a photobiological fuel cell having a voltage of about 0.65 V.

FIG. 7B is a graph illustrating the change of NADH concentration with time in the electrolyte containing ethanol with later addition of an alcohol dehydrogenase (ADH) and aldehyde dehydrogenase (ALDH) as an enzyme system.

In FIG. 7B, the gray empty squares indicate the NADH concentration in the power-generating cell after addition of ethanol, but prior to addition of ADH and ALDH. The NADH concentration is constant. After addition of ADH and ALDH (gray filled squares), the concentration of NADH increases until it approaches a value determined by the amount of electrons taken out by the external circuit and the amount of ethanol and its oxidation product acetaldehyde in the electrolyte. The black empty squares indicate the change of NADH concentration in an electrolyte with ethanol, put in a container free of electrodes, prior to addition of enzymes. The concentration is constant. After addition of ADH and ALDH under the same conditions as in the power-generating cell, the rise in NADH concentration is shown as black filled squares. In FIG. 7B, these latter plots are identified as "Control". Since Control has no electrodes, electrons are not removed by the external circuit. $NAD^+$ in the electrolyte receives electrons from ethanol and acetaldehyde, and is converted to NADH through the mediation of ADH and ALDH. Thus, the concentration of NADH continues to increase with time.

A power-generating cell was formed by an electrolyte 23, an air electrode 27, and an electrolyte containing NADH, $NAD^+$, ethanol, and ADH and ALDH as an enzyme system. When irradiated with sunlight, the power-generating cell operated as a photobiological fuel cell having a voltage of about 0.65 V.

In the present example, tin oxide ($SnO_2$) was used as the oxide semiconductor. The same evaluation could be made with films of particulate $TiO_2$, or other particulate metal oxides such as ZnO and $TiO_2$. $WO_3$ instead of $SnO_2$. The same evaluation could also be made on the compounds P2, P3, P4, P5 and P6 instead of the compound P1 as a photosensitizer compound, which produces an oxidant, and an electron when irradiated with light.

Example 4 of a Photoelectrical Chemical Cell (from Gust et al., WO 03/079480)

A power-generating cell was formed by the same negative electrode 23 as used in Example 1, platinum (Pt) as a counter electrode 24 and a buffer solution having pH 7.3 containing an NAD+/NADH oxidation-reduction mediator in the electrolyte. D-glucose was used as a carbon-containing compound was used. D-glucose-dehydrogenase (GDH) was used as an enzyme.

FIG. 8 is a graph illustrating the relationship between the amount of electrons removed by the external circuit from the electrolyte having GDH added thereto as an enzyme system (abscissa) and the amount of NADH consumed during irradiation with light (ordinate). The symbol ○ indicates the relationship between the amount of NADH consumed and the amount of electrons produced prior to addition of the enzyme, but with D-glucose present. This relationship shows that the amount of NADH consumed and the amount of electrons are proportional to one another, demonstrating that electrons released from NADH are removed by the external circuit. The symbol ● indicates the relationship between the amount of NADH consumed and the amount of electrons produced in the external circuit from the electrolyte after addition of the enzyme system.

Before addition of the enzyme, NADH is consumed and oxidized to $NAD^+$, with the concurrent production of electrons in the external circuit. After addition of the enzyme, NADH is regenerated and the amount apparently consumed drops slightly below the original amount. In other words, NADH releases electrons to form $NAD^+$, which then receives electrons from D-glucose through catalysis by the enzyme to reform NADH. Thus, in the presence of the enzyme, the amount of NADH consumed is kept constant regardless of the number of electrons thus taken out. This state lasts as long as D-glucose is present in the electrolyte.

In the present example, tin oxide ($SnO_2$) was used as the oxide semiconductor. The same evaluation could be made on films of particulate $TiO_2$, and on other particulate metal oxides such as ZnO and $TiO_2$.$WO_3$, instead of $SnO_2$. The same evaluation could also be made on the compounds P2, P3, P4, P5 and P6 instead of the compound P1 as a photosensitizer compound which produces an oxidant and an electron when irradiated with light.

Method for Detection and Quantification of Nicotinamide Adenine Dinucleotide, Reduced Form (NADH) or Nicotinamide Adenine Dinucleotide Phosphate, Reduced Form (NADPH)

Nicotinamide adenine dinucleotide, reduced form (NADH) and nicotinamide adenine dinucleotide phosphate, reduced form (NADPH) are enzyme cofactors that are produced by, or consumed by, a large variety of enzymes. One class of these enzymes act upon substrate molecules, and in concert produce NADH from nicotinamide adenine dinucleotide, oxidized form ($NAD^+$), or NADPH from nicotinamide adenine dinucleotide phosphate, oxidized form ($NADP^+$). Another class act upon substrate molecules, and in concert produce $NAD^+$ from NADH, or $NADP^+$ from NADPH In medical, biological or biotechnological assays, it is useful to detect the amount of NADH or NADPH produced or consumed. By doing so, it is possible to determine the amount of substrate material that was present in the mixture, and consumed by the enzyme. Alternatively, in the presence of an excess of substrate, it is possible to determine the activity and turnover number of the enzyme. The use of NADH or NADPH in such assays requires a convenient, accurate and specific method for determining the amount of NADH or NADPH present in a mixture. The method described here makes such a determination.

The basis of the method is a photoelectrochemical fuel cell. Two generally employed technologies for production of electricity are photovoltaics and fuel cells. Photovoltaics convert light energy into electrical energy. Fuel cells carry out exergonic oxidation and reduction chemical reactions in two half-cells, and use the resulting energy to generate electromotive force and electrical current flowing between an anode and a cathode.

In this invention, these two concepts are combined into a single device for detection and quantification of NADH or NADPH. The device is an electrochemical fuel cell consisting of:

a. An electrochemical half-cell consisting of a dye-sensitized nanoparticulate photoanode operating in an aqueous medium, which contains the reducing agent (analyte) NADH or NADPH that donates electrons into the photo-oxidized dye at the photoanode, thereby being itself oxidized.

b. A second electrochemical half cell consisting of a suitable cathode and associated half-cell reactions, which can be incorporated into the same aqueous medium, or coupled to the photoanode half-cell via a semi-permeable device such as a membrane, frit or salt bridge.

c. An ammeter or other suitable device for detection of electrical current passing between the photoanode and the cathode and the associated voltage.

d. A suitable light source.

The photoanode is illuminated with light. In the absence of NADH or NADPH, no photocurrent flows through the device. When the analyte (NADH or NADPH) is added to the aqueous solution bathing the photoanode, electrical current will flow as the fuel is oxidized. The number of electrons that flow between the photoanode and the cathode, and are detected by the ammeter, is proportional to the number of molecules of NADH or NADPH consumed. In a suitable concentration range, the current flow at a given time after the start of illumination is proportional to the concentration of NADH or NADPH. In all concentration ranges, the total number of electrons flowing through the circuit is proportional to the number of molecules of NADH or NADPH consumed, and therefore present when the illumination was begun. Chemically, two electrons are liberated when one molecule of NADH (NADPH) is oxidized to $NAD^+$ ($NADP^+$).

Details of Half-Cell Function.

A representative photoelectrochemical cell for detection of NADH or NADPH, and illustrating the principles of the invention is show in FIG. 9.

Photoanode. One component of the photoanode is a conductive surface, which may be transparent to light. Indium tin oxide coated glass or indium tin oxide coated fused silica are examples of a transparent conductive material. The surface of this material is covered with a layer of wide band gap semiconductor nanoparticles. Examples of suitable materials are tin dioxide and titanium dioxide. Onto the surface of the nanoparticles is deposited a layer of light-absorbing sensitizer dye (P in FIG. 9). This material absorbs light in spectral regions where the excitation source with which the cell will be used has a significant photon flux. The energies of some of its lowest-lying excited states (singlet, triplet) and its first oxidation potential are such that the singlet or triplet state is energetically capable of injection of an electron into the nanoparticulate surface to generate $P^+$. This event leads to formation of the oxidized sensitizer, $P^+$, and mobile electrons which migrate through the nanoparticulate layer to the conductive surface, and hence into the external electrical circuit. The sensitizer P bears functionality that allows it to bind to the surface of the nanoparticles in a structural arrangement that renders the excited state of P kinetically competent to inject an electron into the nanoparticle layer with suitable efficiency.

Analyte Redox Couple. The redox couple consists of $NADH/NAD^+$ or $NADPH/NADP^+$, depending upon which species is to be detected. As the cell operates, the NADH or NADPH present is converted into $NAD^+$ or $NADP^+$. In the process, two electrons are removed from NADH or NADPH by the oxidized sensitizer $P^+$, regenerating P, and electrons pass through the external circuit. Thus, P is recycled as a photocatalyst, and the electrons flowing through the external circuit are due to oxidation of NADH or NADPH. The number of electrons passing through the circuit is proportional to the amount of NADH or NADPH initially present.

Electrolyte. The half-cell electrolyte (grey area in FIG. 9) is aqueous in nature, providing an environment in which the photoanode and redox couple are capable of functioning as described above. The electrolyte contains any necessary buffers, salts or other substances necessary to ensure stable operation of the cell.

Cathode Half-Cell. The cathode half cell can in principle function either in the electrolyte of the photoanode, or in a separate half-cell compartment. In the latter mode, the cathode half-cell is separated from the photoanode half-cell by a semipermeable membrane, frit, salt bridge, or other charge-transmitting electrochemical device. Its electrode receives electrons from the photoanode via the external circuit and uses these electrons to carry out reduction reactions on a suitable material, generating a more reduced material. Two examples of many suitable cathodic half cells are a $Hg/HgSO_4$ electrode in a saturated potassium sulfate solution separated from the photoanode compartment by a Nafion semipermeable membrane, or a platinum electrode inserted into the electrolyte.

Example 1

The device as described above and FIG. 9, in which the photoanode has a conductive surface of indium-tin oxide deposited on glass, the nanoparticulate layer is tin dioxide, the sensitizer P is porphyrin with the structure P1 (above), and the redox couple/analyte is nicotinamide adenine dinucleotide, reduced form (NADH)/nicotinamide adenine dinucleotide oxidized form ($NAD^+$). P is oxidized to $P^+$ at the surface of the photoanode by photoinduced electron transfer into the nanoparticulate electrode, and $P^+$ is reduced to P by NADH. In this process, $NAD^+$ is ultimately generated through removal of two electrons from NADH and associated chemistry.

Figure 10:
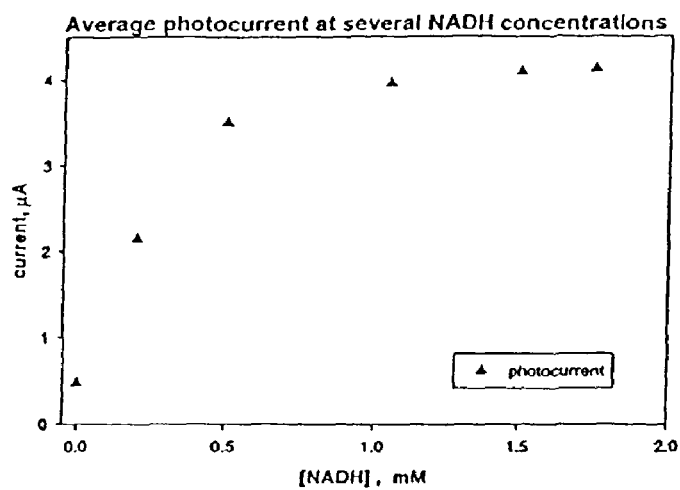
FIG. 10 is a graph showing the average photocurrent in a photoelectrochemical cell at several NADH concentrations.
Figure 11:
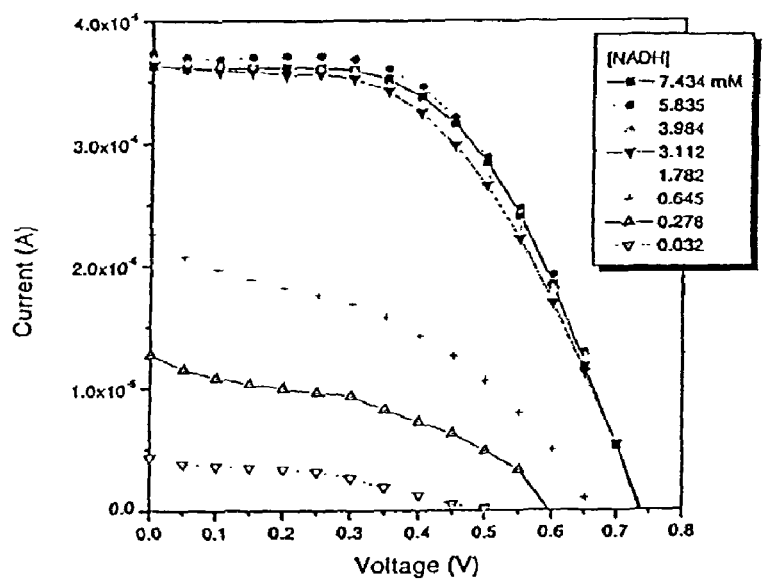
FIG. 11 is a graph showing that the current generated by a photoelectrochemical cell at different applied voltages is proportional to the concentration of NADH initially present, within a range of concentrations.
Figure 12:
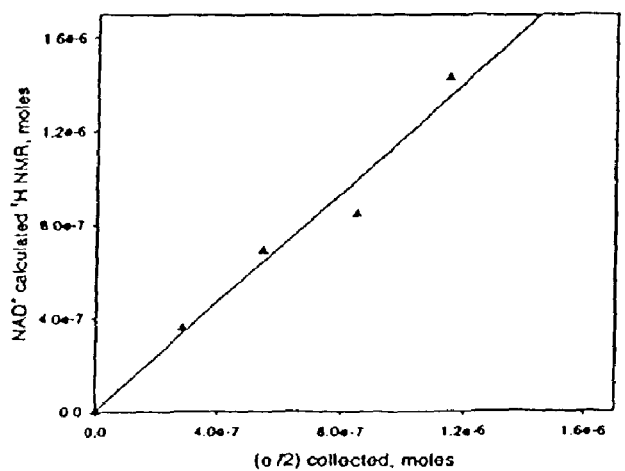
FIG. 12 is a graph showing that every two electrons passing through the external circuit results in the oxidation of one molecule of NADH to one molecule of $NAD^+$, as determined independently by a nuclear magnetic resonance assay of the $NAD^+$ produced.

FIG. 10 shows that under these conditions, the open circuit photocurrent is a function of the initial concentration of NADH. FIG. 11 shows that under these conditions, the current generated by the cell at different applied voltages is proportional to the concentration of NADH initially present, within a certain range of concentrations. FIG. 12 shows that under these conditions, every two electrons passing through the external circuit results in the oxidation of one molecule of NADH to one molecule of $NAD^+$, as determined independently by a nuclear magnetic resonance assay of the $NAD^+$ produced. Thus, the number of electrons passing through the external circuit is equal to one-half the number of NADH molecules oxidized.

Example 2

Figure 13:
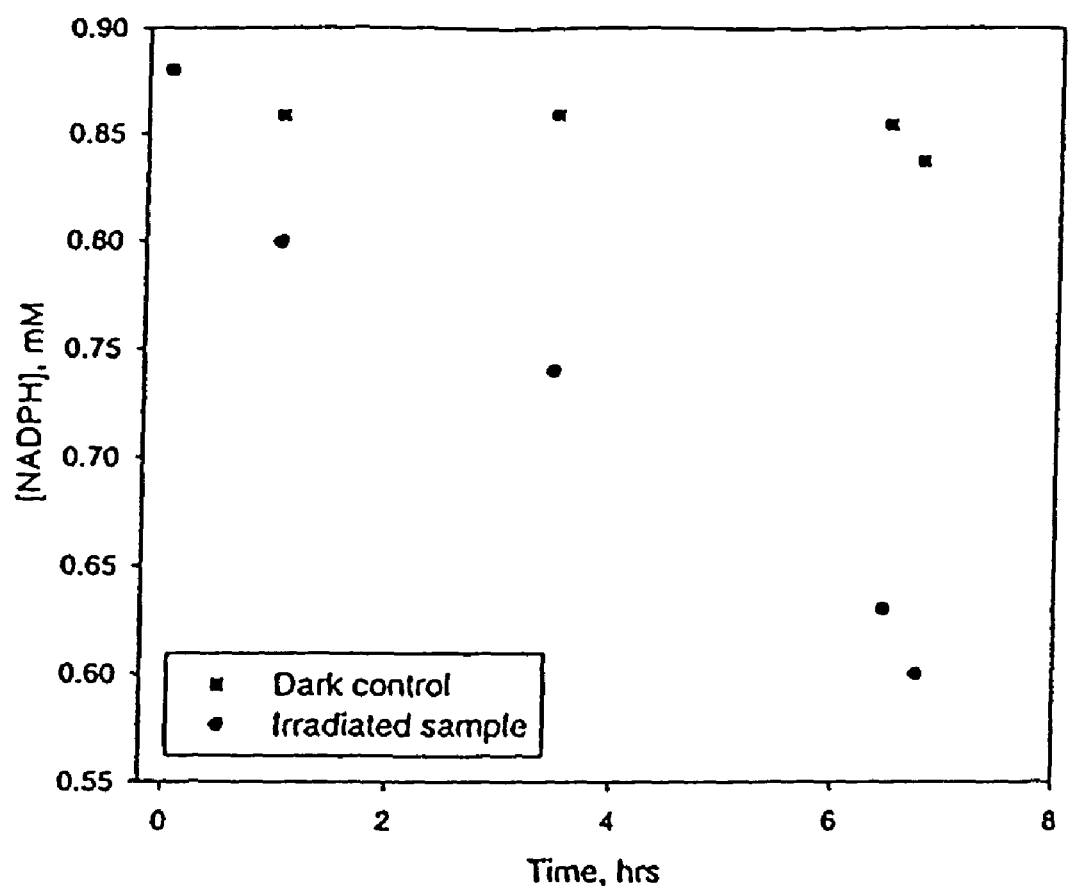
FIG. 13 is a graph showing the consumption of NADPH in a photoelectrochemical cell as a function of time.

The device described in Example 1 immediately above, in which the redox couple is nicotinamide adenine dinucleotide phosphate, reduced form (NADPH)/nicotinamide adenine dinucleotide phosphate oxidized form ($NADP^+$). P is oxidized to $P^+$ at the surface of the photoanode by photoinduced electron transfer into the nanoparticulate electrode, and $P^+$ is reduced to P by NADPH. In this process, $NADP^+$ is ultimately generated. FIG. 13 shows the consumption of NADPH by a cell constituted as described in Example 1 and containing an initial amount of NADPH. The amount of NADPH consumed as the cell operates is proportional to the total number of electrons produced by the cell over a given time period of operation.

The results (not shown) are similar when the device described in Example 1 has a titanium nanoparticulate layer.

Method for Detection and Quantification of Analytes Through the Action of $NADH/NAD^+$- or $NADPH/NADP^+$-Dependent Enzymes and an Associated Photoelectrochemical Measurement)

Natural enzymes catalyze chemical reactions, converting starting materials (substrates) into products with essentially the maximum theoretical yield, and no interfering side reactions. In addition, they are exquisitely specific, in general acting only on a single substrate. These qualities make enzymes attractive components of sensors for specific and sensitive detection of various analytes (substrates) of biomedical, biotechnological, and technological interest. In order to employ enzymes in sensors, however, there must be some method for detection of the conversion of the substrate into product. In principle, this can be done by detecting the product of the reaction in a quantitative fashion. However, this method requires a different detection protocol for each substrate, and detection of the product is not necessarily any simpler than detection of the substrate (analyte). Many enzymes use coenzyme molecules that are consumed during the course of conversion of substrate to product, and converted to a different molecular form. The consumption of the coenzyme is directly proportional to the consumption of the substrate. In such a situation, the amount of substrate (analyte) initially present can be determined from the amount of coenzyme consumed during the enzymatic conversion of substrate to product. Here, the present inventors describe a method for qualitative and quantitative detection of an analyte based on the consumption or production of the coenzymes nicotinamide adenine dinucleotide, reduced form (NADH); nicotinamide adenine dinucleotide phosphate, reduced form (NADPH); nicotinamide adenine dinucleotide, oxidized form ($NAD^+$); or nicotinamide adenine dinucleotide phosphate, oxidized form ($NADP^+$) by the enzyme during the conversion of analyte to product, and subsequent detection of the amount of NADH or NADPH produced or consumed using a photoelectrochemical method.

Nicotinamide adenine dinucleotide, reduced form (NADH) and nicotinamide adenine dinucleotide phosphate, reduced form (NADPH) are coenzymes that are produced by, or consumed by, a large variety of enzymes. One class of these enzymes act upon substrate molecules (analytes), and in concert produce NADH from nicotinamide adenine dinucleotide, oxidized form ($NAD^+$), or NADPH from nicotinamide adenine dinucleotide phosphate, oxidized form ($NADP^+$). Another class act upon substrate (analyte) molecules, and in concert produce $NAD^+$ from NADH, or $NADP^+$ from NADPH. In most cases, one molecule of coenzyme is consumed for each molecule of substrate consumed. Thus, by measuring the amount of coenzyme consumed, it is possible to determine the amount of substrate material that was present in the mixture, and consumed by the enzyme. Previously, detection of these coenzymes has been difficult. Spectrochemical methods are subject to interference at the absorption wavelengths. Electrochemical methods have been hampered by the fact that NADH and -NADPH are not readily and quantitatively oxidized to $NAD^+$ and $NADPH^+$ at the usual electrochemical electrodes. As described above, a photoelectrochemical method has been developed to detect these coenzymes. This embodiment of the present invention uses the methodology described above as a basis for enzymatic sensors for the detection of all enzymes using NADH, NADPH, $NAD^+$ or $NADP^+$ as coenzymes.

The basis of the method is a photoelectrochemical fuel cell. Two generally employed technologies for production of electricity are photovoltaics and fuel cells. Photovoltaics convert light energy into electrical energy. Fuel cells carry out exergonic oxidation and reduction half-cell chemical reactions, and use the resulting energy to generate electromotive force and electrical current flowing between an anode and a cathode. In this invention, these two concepts are combined into a single device for detection and quantification of analytes used as substrates by $NADH/NAD^+$- or $NADPH/NADP^+$-dependent enzymes. The device is an electrochemical fuel cell consisting of:

a. An electrochemical half-cell consisting of a dye-sensitized nanoparticulate photoanode operating in an aqueous medium, which contains the reducing agent (coenzyme) NADH or NADPH that donates electrons into the photooxidized dye at the photoanode, thereby being itself oxidized. Alternatively, the solution may contain $NAD^+$ or $NADP^+$ that will be enzymatically converted to NADH or NADPH. In addition, the photoanode compartment contains a suitable enzyme that uses the desired analyte as substrate and NADH, $NAD^+$, NADPH, or $NADP^+$ as a coenzyme.

b. A second electrochemical half cell consisting of a suitable cathode and associated half-cell reactions, which can be incorporated into the same aqueous medium, or coupled to the photoanode half-cell via a semi-permeable device such as a membrane, frit or salt bridge.

c. An ammeter or other suitable device for detection of electrical current passing between the photoanode and the cathode, and the associated voltage.

d. A suitable light source.

When the photoanode is illuminated with light, no photocurrent flows through the device in the absence of NADH or NADPH. When NADH or NADPH is added to the aqueous solution bathing the photoanode, electrical current will flow as the fuel is oxidized. The number of electrons that flow between the photoanode and the cathode, and are detected by the ammeter, is proportional to the number of molecules of NADH or NADPH consumed. In a suitable concentration range, the current flow at a given time after the start of illumination is proportional to the concentration of NADH or NADPH. In all concentration ranges, the total number of electrons flowing through the circuit is proportional to the number of molecules of NADH or NADPH consumed, and therefore present when the illumination was begun. Chemically, two electrons are liberated when one molecule of NADH (NADPH) is oxidized to $NAD^+$ ($NADP^+$).

Use with NADH or NADPH Producing Reactions.

The cell as described above is prepared containing $NAD^+$ (or $NADP^+$) and a suitable enzyme in a suitable buffer solution as the electrolyte. The cell is illuminated. No steady-state photocurrent is observed because no NADH or NADPH is present. Mumination is stopped, and the material to be analyzed (containing enzyme substrate) is added to the cell, whereupon the enzyme converts the substrate to product, and simultaneously and proportionately converts $NAD^+$ (or $NADP^+$) to NADH (or NADPH). The cell is again illuminated, and the photocurrent measured. The initial level of the photocurrent will be proportional to the NADH (or NADPH) concentration in the electrolyte, and therefore to the amount of analyte present in the initial sample and acted upon by the enzyme. If irradiation is continued until the photocurrent returns to zero, the total number of electrons passing through the circuit as a result of photocurrent is proportional to the total amount of NADH (or NADPH) consumed, and therefore to the total amount produced, and therefore to the total amount of substrate analyte originally present.

Use with NADH or NADPH Consuming Reactions.

The cell as described above is prepared containing NADH (or NADPH) and a suitable enzyme in a suitable buffer solution as the electrolyte. The cell is illuminated, and the initial photocurrent is measured. This photocurrent is proportional to the amount of NADH (or NADPH) initially present. The light is shut off, and the mixture containing the analyte (enzyme substrate) is added. The enzyme converts the substrate to product, and in the process consumes a proportionate amount of NADH (or NADPH). When enzymatic action is complete, the light is turned on, and the initial photocurrent measured. The initial level of the photocurrent will be proportional to the NADH (or NADPH) concentration remaining in the electrolyte. The reduction in photocurrent (relative to the current before introduction of the analyte (substrate) will be proportional to the amount of analyte present in the initial sample and acted upon by the enzyme. If irradiation is continued until the photocurrent goes to zero, the total number of electrons passing through the circuit as a result of photocurrent is proportional to the total amount of NADH (or NADPH) consumed by the photoelectrochemical cell. The difference between this amount and the amount of NADH (or NADPH) present before addition of the analyte (substrate) will be proportional to the amount of NADH (or NADPH) consumed by the enzyme, and thus proportional to the amount of analyte (substrate) added to the cell.

Details of Half-Cell Function.

Figure 14:
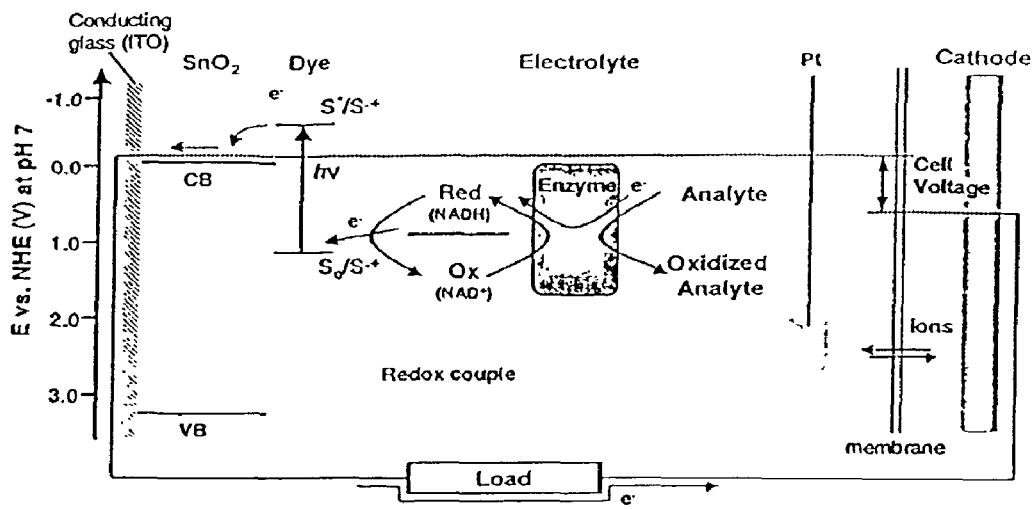
FIG. 14 is a schematic diagram illustrating a photoelectrochemical cell useful for the detection and quantification of analytes which are substrates for enzymes which reduce $NAD^+$ to NADH during consumption of the analyte.

A representative photoelectrochemical cell illustrating the principles of the invention is show in FIG. 14, for the case where the enzyme reduces NAD+ to NADH during consumption of the analyte (substrate).

Photoanode. One component of the photoanode is a conductive surface, which may be transparent to light. Indium tin oxide coated glass or indium tin oxide coated fused silica are examples of a transparent conductive material. The surface of this material is covered with a layer of wide band gap semiconductor nanoparticles. Examples of suitable materials are tin dioxide and titanium dioxide. Onto the surface of the nanoparticles is deposited a layer of light-absorbing sensitizer dye (S in FIG. 14). This material absorbs light in spectral regions where the excitation source with which the cell will be used has a significant photon flux. The energies of some of its lowest-lying excited states (singlet, triplet) and its first oxidation potential are such that the singlet or triplet state is energetically capable of injection of an electron into the nanoparticulate surface to generate $S^+$. This event leads to formation of the oxidized sensitizer, $S^+$, and mobile electrons which migrate through the nanoparticulate layer to the conductive surface, and hence into the external electrical circuit. The sensitizer S bears functionality that allows it to bind to the surface of the nanoparticles in a structural arrangement that renders the excited state of S kinetically competent to inject an electron into the nanoparticle layer with suitable efficiency.

Redox Couple. The redox couple consists of $NADH/NAD^+$ or $NADPH/NADP^+$, depending upon the particular enzyme and analyte combination of interest. As the cell operates, any NADH or NADPH present (whether generated by the enzyme or added at the beginning of the assay) is converted into $NAD^+$ or $NADP^+$. In the process, two electrons are removed from NADH or NADPH by the oxidized sensitizer $S^+$, regenerating S, and electrons pass through the external circuit. Thus, S is recycled as a photocatalyst, and the electrons flowing through the external circuit are due to oxidation of NADH or NADPH. The number of electrons passing through the circuit is proportional to the amount of NADH or NADPH initially present.

Electrolyte. The half-cell electrolyte is aqueous in nature, providing an environment in which the photoanode, redox couple, and enzyme-substrate combination are capable of functioning as described above. The electrolyte contains any necessary buffers, salts, activators or other substances necessary to ensure operation of the cell.

Enzyme and Substrate. In principle, any enzyme capable of producing NADH or NADPH from $NAD^+$, or $NADP^+$ as coenzymes, or of consuming NADH or NADPH, is suitable for use in this assay method. Examples are the various dehydrogenase enzymes, but the utility of this method is not limited to this class of enzymes. Others will be appreciated by those skilled in the art. Combinations of enzymes may also be used. The choice of enzyme or enzymes for a particular assay is determined by the nature of the analyte (substrate). A few examples of substrates include, but are not limited to, sugars including glucose, starches, other carbohydrates, fats, hydrocarbons, alcohols including ethanol and methanol, aldehydes including acetaldehyde, and acids including acetic acid.

Cathode Half-Cell. The cathode half cell can in principle function either in the electrolyte of the photoanode (such as the platinum electrode indicated in FIG. 14), or in a separate half-cell compartment (such as the cathode shown in FIG. 14). In the latter mode, the cathode half-cell is separated from the photoanode half-cell by a semipermeable membrane, frit, salt bridge, or other charge-transmitting electrochemical device. Its electrode receives electrons from the photoanode via the external circuit and uses these electrons to carry out reduction reactions on a suitable material, generating a more reduced material. Two examples of many suitable cathodic half cells are a $Hg/Hg_2SO_4$ electrode in a saturated potassium sulfate solution separated from the photoanode compartment by a Nafion semipermeable membrane, or a platinum electrode inserted into the electrolyte.

Example 3

Figure 15:
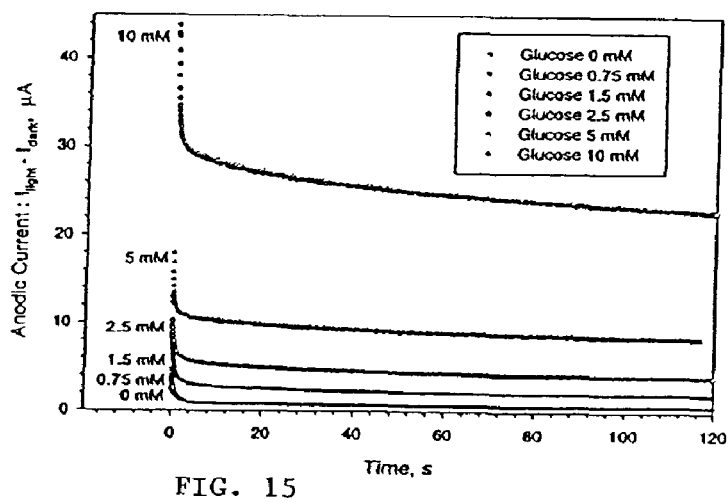
FIG. 15 is a graph showing that the photocurrent in the photoelectrochemical cell at a given time is proportional to the initial concentration of the analyte (β-D-glucose).

The device as described above and FIG. 14, in which the photoanode has a conductive surface of indium-tin oxide deposited on glass, the nanoparticulate layer is tin dioxide, the sensitizer S is a porphyrin with the structure P1 (above), and the redox couple/analyte is nicotinamide adenine dinucleotide, reduced form (NADH)/nicotinamide adenine dinucleotide oxidized form (NAD+). The enzyme is glucose dehydrogenase (GDH), and the analyte is β-D-glucose. The performance of this device, which illustrates the method claimed, is shown in FIG. 15. When there is no β-D-glucose present, illumination of the device produced no steady-state photocurrent, because no NADH is present. When the light is turned off and β-D-glucose is added, the following set of reactions occurs. The enzyme GDH converts all of the β-D-glucose present to its oxidation product, and for every molecule of β-D-glucose consumed, one molecule of $NAD^+$ is converted to NADH. When this reaction is complete, the light is again turned on. S is oxidized to $S^+$ at the surface of the photoanode by photoinduced electron transfer into the nanoparticulate electrode, and the electrons migrate through the photoanode and the external circuit to the cathode. They are detected as current and voltage. The $S^+$ thus produced is reduced to S by NADH. In this process, $NAD^+$ is ultimately generated through removal of two electrons from NADH and associated chemistry.

Figure 16:
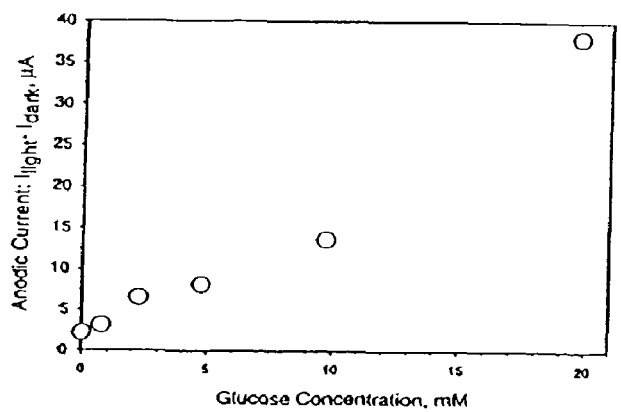
FIG. 16 is a graph showing photocurrent as a function of the total initial glucose concentration.

As shown in FIG. 15, the photocurrent at a given time is proportional to the initial concentration of β-D-glucose in the solution. Thus, by proper calibration, the photocurrent at a given time can be used to determine the amount of β-D-glucose originally present, and consumed, in the electrolyte solution. This is illustrated by FIG. 16, which shows the photocurrent as a function of the total initial glucose concentration. If the cell had been operated until all of the NADH produced by the enzyme was consumed by the photoanode, then the total number of electrons passing through the circuit would equal twice the total number of NADH molecules consumed by the photoanode, and therefore twice the total number of β-D-glucose molecules consumed by the enzyme.

Example 4

Figure 17:
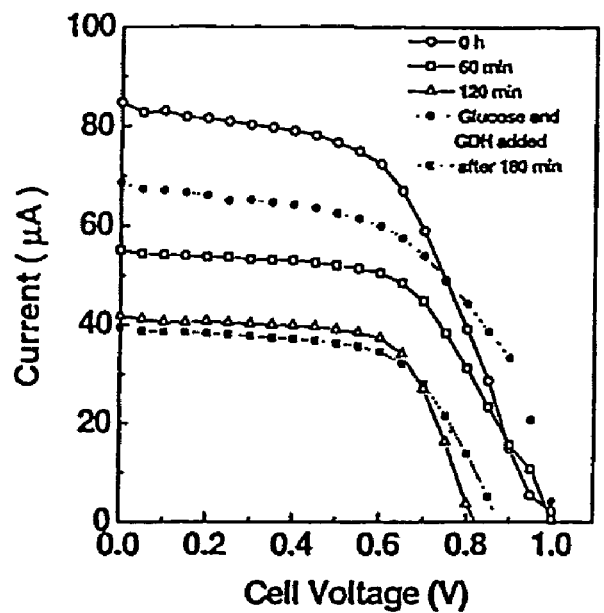
FIG. 17 is a graph showing that the electrical output of a photoelectrochemical cell is sensitive to the production of NADH from $NAD^+$ occurring when GDH enzyme converts analyte β-D-glucose to its oxidation product.

The device described Example 3, in which the nanoparticulate layer is $TiO_2$. FIG. 17 shows the operation of this cell. The experiment begins with 5 mM NADH in the electrolyte. After operating with illumination for 120 min, a substantial amount of the NADH has been converted to $NAD^+$ by oxidation at the photoanode. At this time, the enzyme GDH is added, and the electrolyte is made 0.1 M in β-D-glucose. The cell current and voltage increase, due to the production of NADH in the electrolyte through the action of the enzyme GDH on the analyte β-D-glucose, with NAD+ as the coenzyme. This experiment shows that the electrical output of the cell is sensitive to the production of NADH from $NAD^+$ which occurs when the enzyme converts analyte β-D-glucose to its oxidation product.

Example 5

Figure 18:
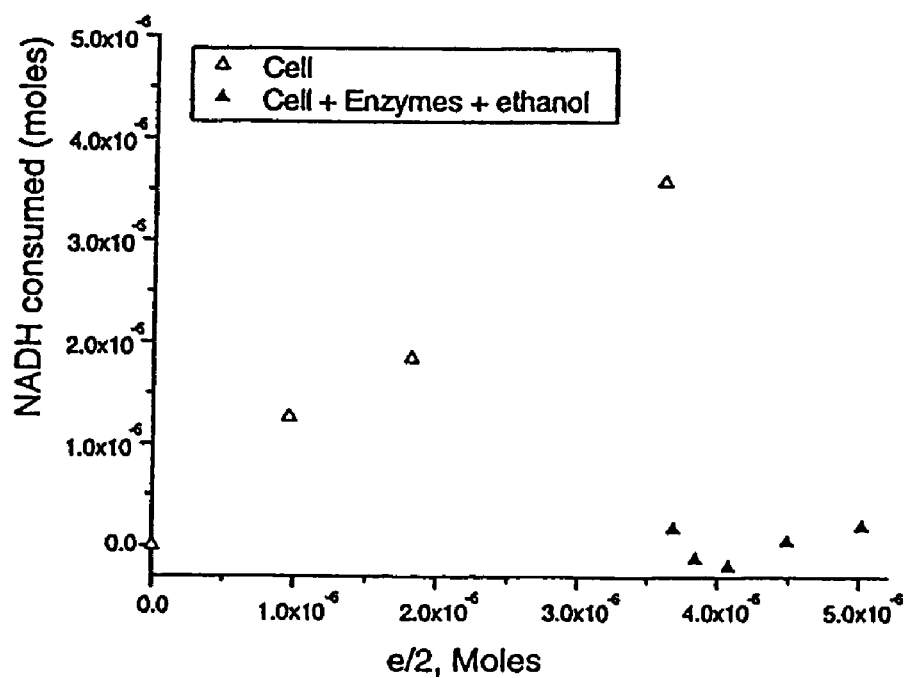
FIG. 18 is a graph showing that the cell consumes NADH while producing current in the external circuit and $NAD^+$ in the electrolyte, and that operation of the enzyme system converts the analyte ethanol into its oxidation products, concurrently producing NADH, which is used to generate current in the external circuit, giving a sensor response.

The device described in Example 3, in which the analyte is ethanol and the enzymes are yeast alcohol dehydrogenase and aldehyde dehydrogenase. In the experiment whose results are shown in FIG. 18, the cell without the enzymes and ethanol is operated in the light until a substantial fraction of NADH is consumed by the electrode, and converted to NAD+, with the production of electrons in the external circuit. At this time, the enzymes and ethanol were added. After addition, the enzymes converted ethanol first to acetaldehyde, and then to acetate. At each step in this oxidation, one molecule of $NAD^+$ was converted to one molecule of NADH. When all of the $NAD^+$ had been converted, the NADH concentration returned to its initial value. This demonstrates that the cell consumes NADH while producing current in the external circuit and $NAD^+$ in the electrolyte, and that the operation of the enzyme system converts the analyte ethanol into its oxidation products, concurrently producing NADH which is used to generate current in the external circuit, giving a sensor response.

Example 6

Figures 19, 20:
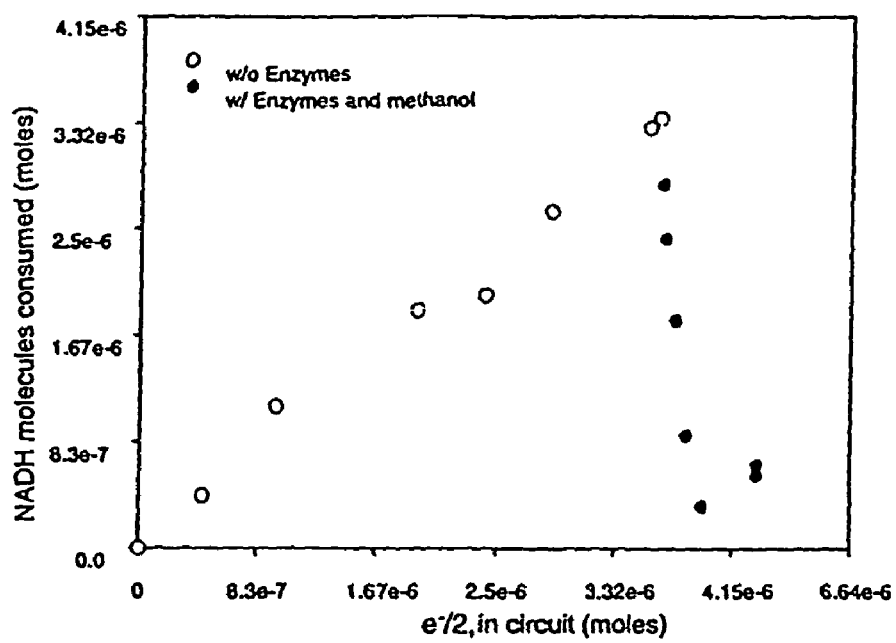
FIG. 19 is a graph showing that the cell consumes NADH while producing current in the external circuit and $NAD^+$ in the electrolyte, and that operation of the enzyme system converts the analyte methanol into its oxidation products, concurrently producing NADH, which is used to generate current in the external circuit, giving a sensor response.
FIG. 20 is a graph showing that the cell consumes NADPH while producing current in the external circuit and $NADP^+$ in the electrolyte, and that operation of the enzyme system converts the analyte β-D-glucose-6-phosphate into its oxidation products, concurrently producing NADPH, which is used to generate current in the external circuit, giving a sensor response.

The device described in Example 5, in which the analyte is methanol and the enzymes are yeast alcohol dehydrogenase, aldehyde dehydrogenase, and formate dehydrogenase. In the experiment whose results are shown in FIG. 19, the cell without the enzymes and methanol is operated in the light until a substantial fraction of NADH is consumed by the electrode, and converted to $NAD^+$, with the production of electrons in the external circuit. At this time, the enzymes and methanol were added. After addition, the enzymes converted methanol first to formaldehyde, then to formate, and finally to carbon dioxide. At each step in this oxidation, one molecule of $NAD^+$ was converted to one molecule of NADH. When all of the $NAD^+$ had been converted, the NADH concentration returned to its initial value. This demonstrates that the cell consumes NADH while producing current in the external circuit and $NAD^+$ in the electrolyte, and that the operation of the enzyme system converts the analyte methanol into its oxidation products, concurrently producing NADH, which is used to generate current in the external circuit, giving a sensor response.

Example 7

The device described in Example 5, in which the analyte is β-D-glucose-6-phosphate, the enzyme is glucose-6-phosphate dehydrogenase, and the redox couple is NADPH/$NADP^+$. In the experiment whose results are shown in FIG. 20, the cell without the enzyme and the analyte is operated in the light until a substantial fraction of NADPH is consumed by the electrode, and converted to $NADP^+$, with the production of electrons in the external circuit. At this time, the enzyme and β-D-glucose-6-phosphate were added. After addition, the enzyme converted β-D-glucose-6-phosphate to gluconolactone-6-phosphate, which hydrolyzed to 6-phosphogluconate. In this oxidation, one molecule of $NADP^+$ was converted to one molecule of NADPH. When all of the $NADP^+$ had been converted, the NADPH concentration returned to its initial value. This demonstrates that the cell consumes NADPH while producing current in the external circuit and $NADP^+$ in the electrolyte, and that the operation of the enzyme converts the analyte (β-D-glucose-6-phosphate into its oxidation products, concurrently producing NADPH, which is used to generate current in the external circuit, giving a sensor response.

Example 8

Figure 21:
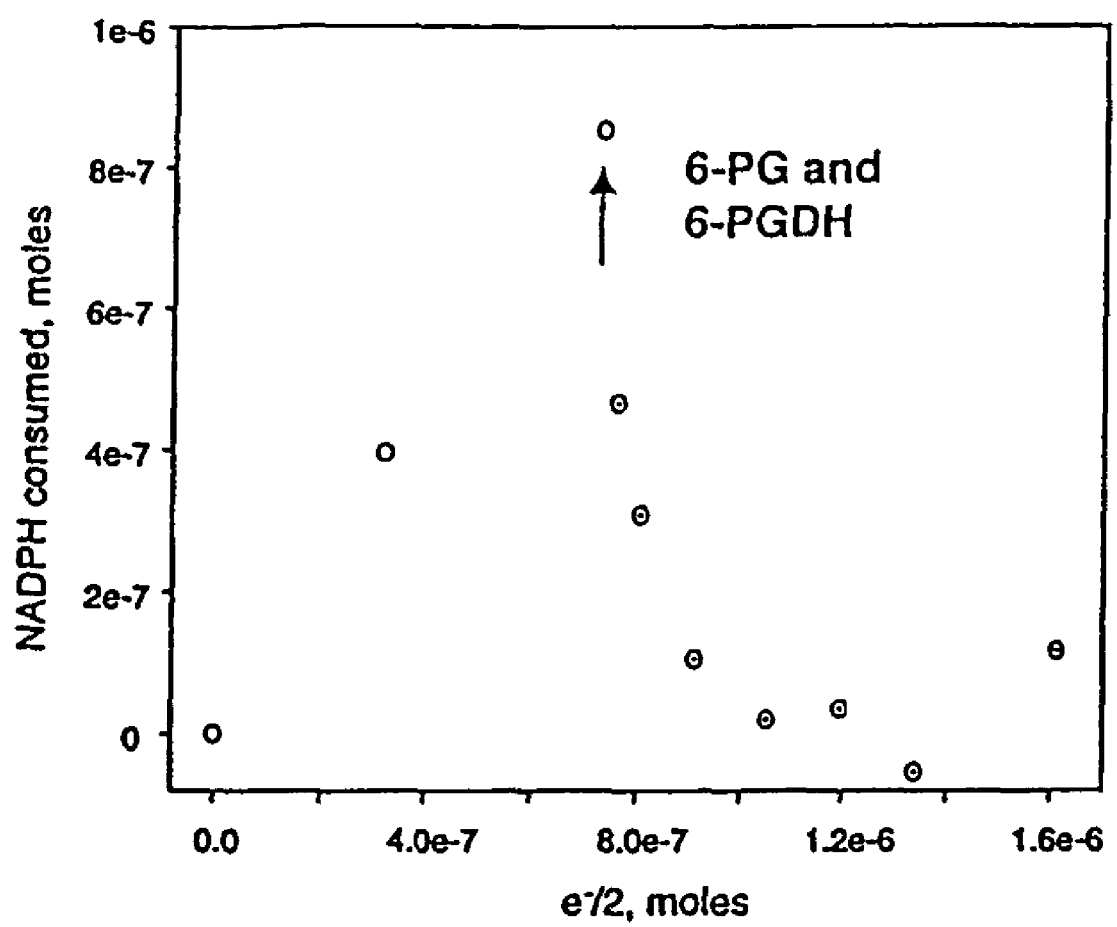
FIG. 21 is a graph showing that the cell consumes NADPH while producing current in the external circuit and $NADP^+$ in the electrolyte, and that operation of the enzyme system converts the analyte 6-phosphogluconate into its oxidation products, concurrently producing NADPH, which is used to generate current in the external circuit, giving a sensor response.

The device described in Example 7, in which the analyte is 6-phosphogluconate and the enzyme is 6-phosphogluconate dehydrogenase. In the experiment whose results are shown in FIG. 21, the cell without the enzyme and 6-phosphogluconate is operated in the light until a substantial fraction of NADPH is consumed by the electrode, and converted to $NADP^+$, with the production of electrons in the external circuit. At this time, the enzyme and 6-phosphogluconate were added. After addition, the enzyme converted 6-phosphogluconate to ribulose-5-phosphate. In this oxidation, one molecule of $NADP^+$ was converted to one molecule of NADPH When all of the $NADP^+$ had been converted, the NADPH concentration returned to its initial value. This demonstrates that the cell consumes NADPH while producing current in the external circuit and $NADP^+$ in the electrolyte, and that the operation of the enzyme converts the analyte 6-phosphogluconate into its oxidation product, concurrently producing NADPH, which is used to generate current in the external circuit, giving a sensor response.

While this invention is described in detail with reference to a certain preferred embodiments, it should be appreciated that the present invention is not limited to those precise embodiments. Rather, in view of the present disclosure which describes the current best mode for practicing the invention, many modifications and variations would present themselves to those of skill in the art without departing from the scope and spirit of this invention. In particular, it is to be understood that this invention is not limited to the particular methodology, protocols, cell lines, animal species or genera, constructs, and reagents described as such may vary, as will be appreciated by one of skill in the art.

What is claimed is:

1. A method for detecting and quantifying the amount of NADH in a mixture, comprising the steps of:
    providing an electrochemical fuel cell comprising:
        a. a first electrochemical half-cell comprising a dye-sensitized nanoparticulate photoanode operating in an aqueous medium and NADH;
        b. a second electrochemical half cell comprising a suitable cathode;
        c. a device for detection of electrical current passing between the photoanode and the cathode and the associated voltage; and
        d. a suitable light source;
    illuminating the photoanode with light;
    consuming the NADH by the electrochemical fuel cell;
    detecting a photocurrent flowing through the device; and
    quantifying the amount of NADH.

2. The method of claim 1, wherein the nanoparticulate photo anode comprises tin dioxide.

3. The method of claim 1, wherein the nanoparticulate photoanode comprises titanium dioxide.

4. The method of claim 1, wherein the cathode is incorporated into the same aqueous medium as the photoanode half-cell.

5. The method of claim 1, wherein the cathode is coupled to the photo anode half-25 cell via a semi-permeable device.

6. The method of claim 5, wherein the semi-permeable device is selected from the group consisting of a membrane, frit or salt bridge.

7. The method of claim 1, wherein the device for detection of electrical current is an ammeter.

8. A method for detecting and quantifying the amount of NADPH in a mixture, comprising the steps of:
    providing an electrochemical fuel cell comprising:
        a. a first electrochemical half-cell comprising a dye-sensitized nanoparticulate photoanode operating in an aqueous medium and NADPH;

b. a second electrochemical half cell comprising a suitable cathode;
c. a device for detection of electrical current passing between the photoanode and the cathode and the associated voltage; and
d. a suitable light source;

illuminating the photoanode with light;
consuming the NADPH by the electrochemical fuel cell;
detecting a photocurrent flowing through the device; and
quantifying the amount of NADPH.

9. The method of claim 8, wherein the nanoparticulate photoanode comprises tin dioxide.

10. The method of claim 8, wherein the nanoparticulate photoanode comprises titanium dioxide.

11. The method of claim 8, wherein the cathode is incorporated into the same aqueous medium as the photoanode half-cell.

12. The method of claim 8, wherein the cathode is coupled to the photo anode halfcell via a semi-permeable device.

13. The method of claim 12, wherein the semi-permeable device is selected from the group consisting of a membrane, frit or salt bridge.

14. The method of claim 8, wherein the device for detection of electrical current is an ammeter.

15. A method for detecting and quantifying the amount of an analyte used as a substrate by an NAD+-dependent enzyme, comprising the steps of:
providing an electrochemical fuel cell comprising:
a. a first electrochemical half-cell comprising a dye-sensitized nanoparticulate photoanode operating in an aqueous medium, which contains NAD+ and an enzyme that uses the analyte of interest as a substrate;
b. a second electrochemical half cell comprising a cathode;
c. an ammeter or other suitable device for detection of electrical current passing between the photoanode and the cathode and the associated voltage; and
d. a suitable light source;
illuminating the photoanode with light;
detecting a first photocurrent flowing through the device;
adding the analyte to the photoanode;
illuminating the photoanode with light;
consuming the NAD+ by the electrochemical fuel cell;
detecting a second photocurrent flowing through the device; and
quantifying the amount of analyte.

16. A method for detecting and quantifying the amount of an analyte used as a substrate by an NADP+-dependent enzyme, comprising the steps of:
providing an electrochemical fuel cell comprising:
a. a first electrochemical half-cell comprising a dye-sensitized nanoparticulate photoanode operating in an aqueous medium, which contains NADP+ and an enzyme that uses the analyte of interest as a substrate;
b. a second electrochemical half cell comprising a cathode;
c. an ammeter or other suitable device for detection of electrical current passing between the photoanode and the cathode and the associated voltage; and
d. a suitable light source;
illuminating the photoanode with light;
detecting a first photocurrent flowing through the device;
adding the analyte to the photo anode;
illuminating the photoanode with light;
consuming the NADP+ by the electrochemical fuel cell;
detecting a second photocurrent flowing through the device; and
quantifying the amount of analyte.

17. A method for detecting and quantifying the amount of an analyte used as a substrate by an NADH-dependent enzyme, comprising the steps of:
providing an electrochemical fuel cell comprising:
a. a first electrochemical half-cell comprising a dye-sensitized nanoparticulate photoanode operating in an aqueous medium, which contains NADH and an enzyme that uses the analyte of interest as a substrate;
b. a second electrochemical half cell comprising a suitable cathode;
c. an ammeter or other suitable device for detection of electrical current passing between the photoanode and the cathode and the associated voltage; and
d. a suitable light source;
illuminating the photoanode with light;
detecting a first photocurrent flowing through the device;
adding the analyte to the photoanode;
illuminating the photoanode with light;
consuming the NADH by the electrochemical fuel cell;
detecting a second photocurrent flowing through the device; and
quantifying the amount of analyte.

18. A method for detecting and quantifying the amount of an analyte used as a substrate by an NADPH-dependent enzyme, comprising the steps of:
providing an electrochemical fuel cell comprising:
a. a first electrochemical half-cell comprising a dye-sensitized nanoparticulate photoanode operating in an aqueous medium, which contains NADPH and an enzyme that uses the analyte of interest as a substrate;
b. a second electrochemical half cell comprising a suitable cathode;
c. an ammeter or other suitable device for detection of electrical current passing between the photoanode and the cathode and the associated voltage; and
d. a suitable light source;
illuminating the photoanode with light;
detecting a first photocurrent flowing through the device;
adding the analyte to the photoanode;
illuminating the photoanode with light;
consuming the NADPH by the electrochemical fuel cell;
detecting a second photocurrent flowing through the device; and
quantifying the amount of analyte.

* * * * *